US008535657B2

(12) United States Patent
Rivero et al.

(10) Patent No.: US 8,535,657 B2
(45) Date of Patent: Sep. 17, 2013

(54) STABILIZED PHARMACEUTICAL FORMULATIONS THAT CONTAIN THE INTERFERONS GAMMAS AND ALPHA IN SYNERGISTIC PROPORTIONS

(75) Inventors: Iraldo Bello Rivero, Cuidad de la Habana (CU); Pedro Lopez Saura, Cuidad de la Habana (CU); Yanelda Garcia Vega, Cuidad de la Habana (CU); Hector Santana Milian, Cuidad de la Habana (CU); Ana Aguilera Barreto, Cuidad de la Habana (CU); Rolando Paez Meireles, Cuidad de la Habana (CU); Lorenzo Anasagasti Angulo, Cuidad de la Habana (CU)

(73) Assignee: Centro de Ingenieria Genetica y Biotecnologia, Havana (CU)

( * ) Notice: Subject to any disclaimer, the term of this patent is extended or adjusted under 35 U.S.C. 154(b) by 386 days.

(21) Appl. No.: 12/092,440

(22) PCT Filed: Oct. 27, 2006

(86) PCT No.: PCT/CU2006/000011
§ 371 (c)(1),
(2), (4) Date: Oct. 1, 2008

(87) PCT Pub. No.: WO2007/051431
PCT Pub. Date: May 10, 2007

(65) Prior Publication Data
US 2009/0304628 A1 Dec. 10, 2009

(30) Foreign Application Priority Data
Nov. 2, 2005 (CU) ................... 2005-0213

(51) Int. Cl.
*A61K 38/21* (2006.01)
*A61K 38/00* (2006.01)
(52) U.S. Cl.
USPC ........ 424/85.4; 424/85.5; 424/85.7; 514/19.3

(58) Field of Classification Search
None
See application file for complete search history.

(56) References Cited

U.S. PATENT DOCUMENTS

| 4,847,079 | A | * | 7/1989 | Kwan | 424/85.7 |
|---|---|---|---|---|---|
| 4,895,716 | A | | 1/1990 | Goldstein et al. | |
| 5,935,566 | A | * | 8/1999 | Yuen et al. | 424/85.7 |
| 5,955,427 | A | * | 9/1999 | McGregor et al. | 514/2.4 |
| 6,887,462 | B2 | * | 5/2005 | Shirley et al. | 424/85.6 |
| 7,067,546 | B2 | * | 6/2006 | Hashimoto et al. | 514/381 |
| 2003/0129162 | A1 | * | 7/2003 | Lau et al. | 424/85.5 |

FOREIGN PATENT DOCUMENTS

| EP | 0276120 A2 | 7/1988 |
|---|---|---|
| WO | WO2004078207 A1 | 9/2004 |

OTHER PUBLICATIONS

Interimmune product insert for Actimmune (2009).*
Schwaab et al., "A Randomized Phase II Trial Comparing Two Different Sequence Combinations of Autologous Vaccine and Human Recombinant Interferon γ and Human Recombinant Interferon α2B Therapy in Patients with Metastatic Renal Cell Carcinoma: Clinical Outcome and Analysis of Immunological Parameters" Journal of Urology, vol. 163, p. 1322-1327 (2000).
Ishii Y, et al., "The Synergistic Effect of Human Recombinant Interferon-Alpha-2-Alpha in Combination with Interferon-Gamma and the Induction of Interferon-Alpha-2-Alpha Receptor by Interferon-Gamma", Journal of Pharmacobio-Dynamics, vol. 12, No. 5, p. 299-304 (1989).

* cited by examiner

*Primary Examiner* — Christine J Saoud
*Assistant Examiner* — Jegatheesan Seharaseyon
(74) *Attorney, Agent, or Firm* — Hoffmann & Baron, LLP

(57) ABSTRACT

The present invention is related to stable pharmaceutical formulations to be applied by parenteral (liquids or freeze-dried), or topic way (gel, unguent or cream) that contain different quantities of the recombinant interferons gamma and alpha in synergistic proportions for the treatment of pathological events that contemplate the malignant or benign not-physiological growth of cells in tissue or organs.

7 Claims, 6 Drawing Sheets

Figure #1.
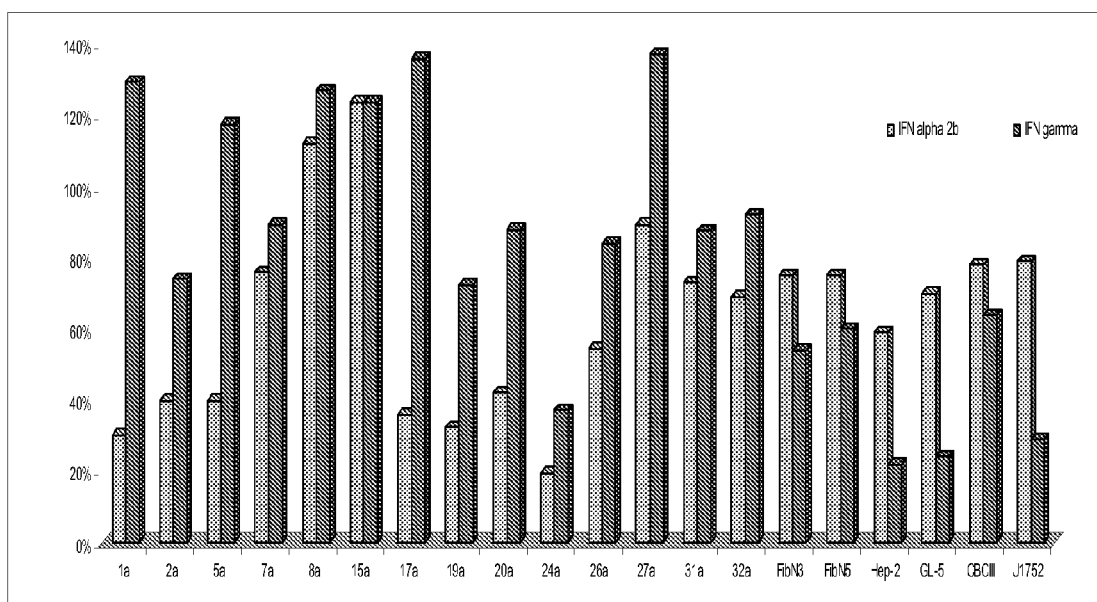

Figure #2
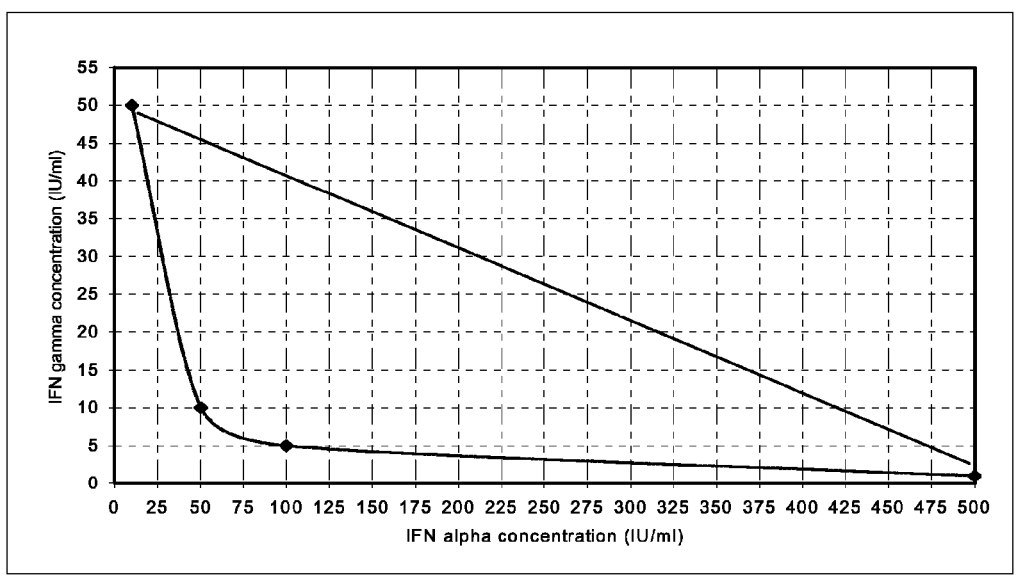

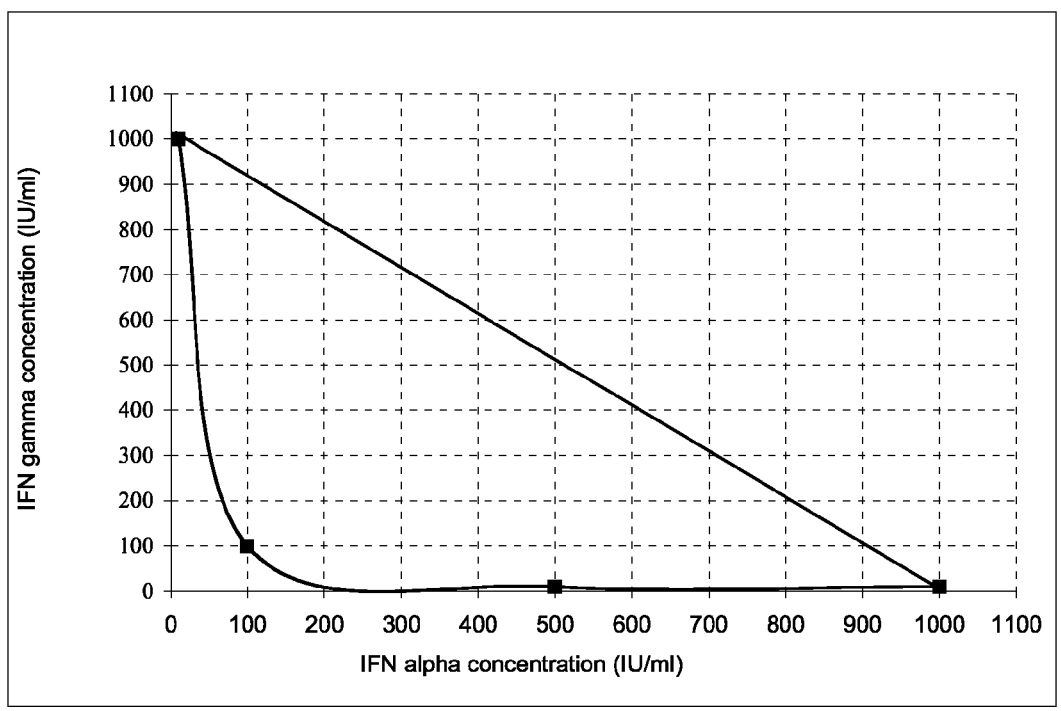
Figure #3

Figure #4
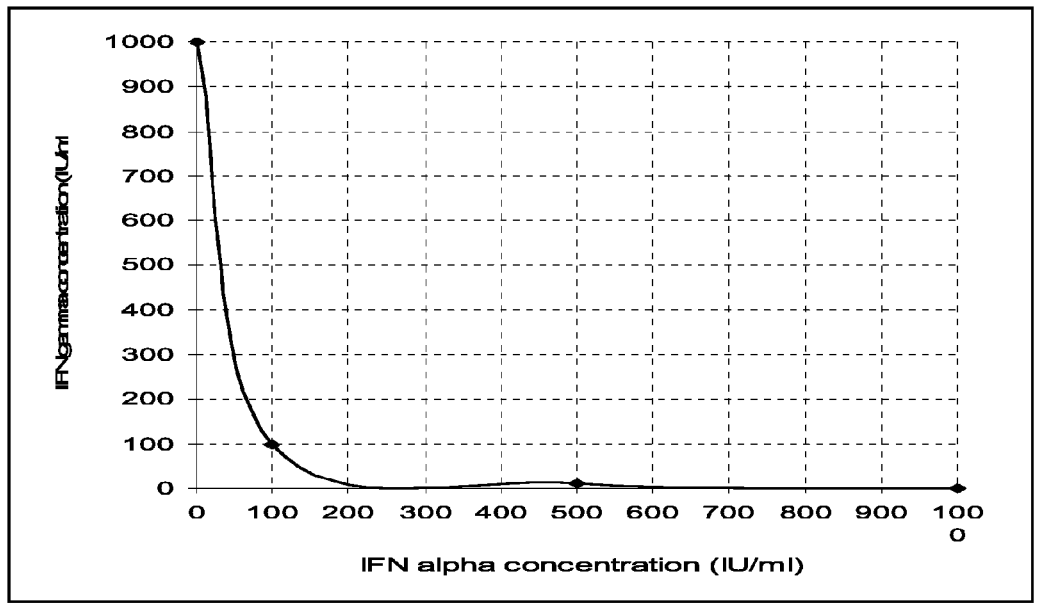
Figure #5
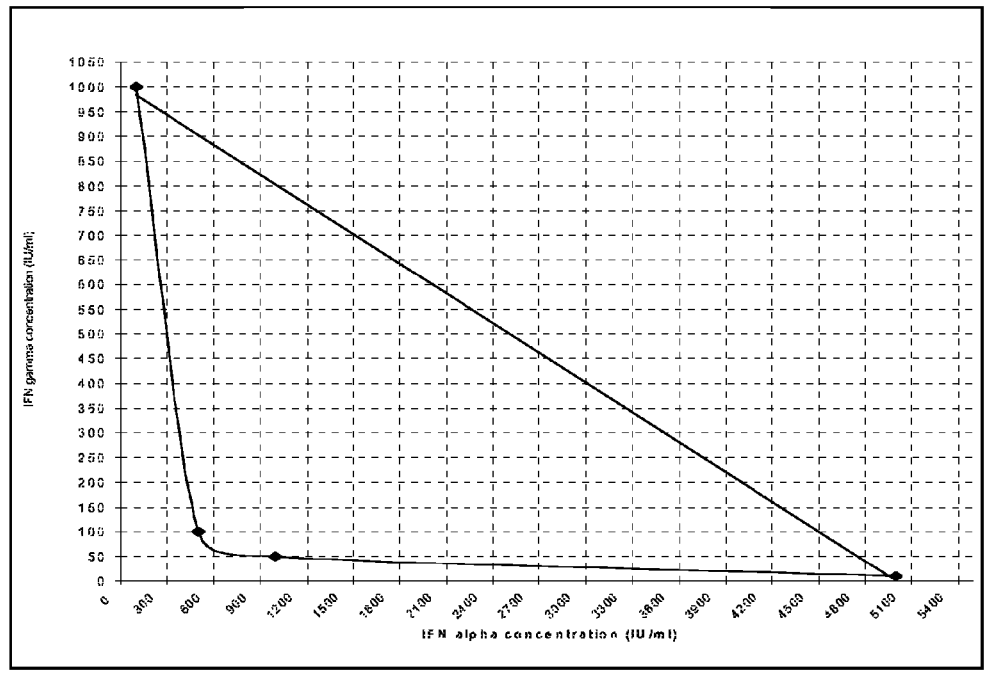

Figure #6
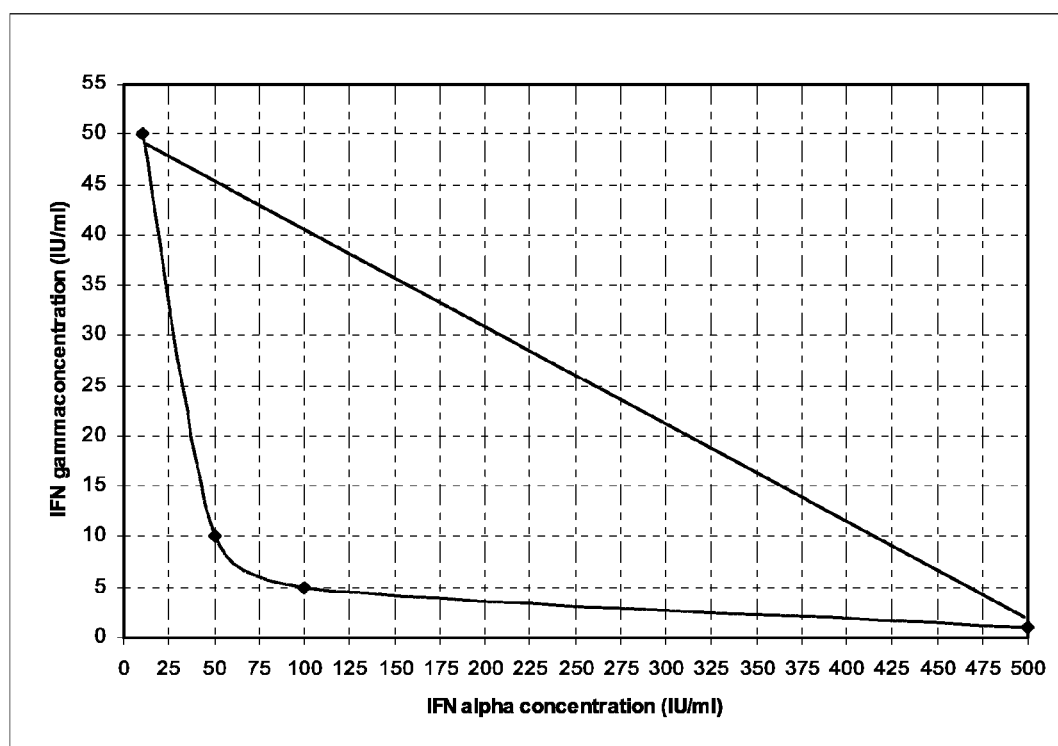

Figure #7
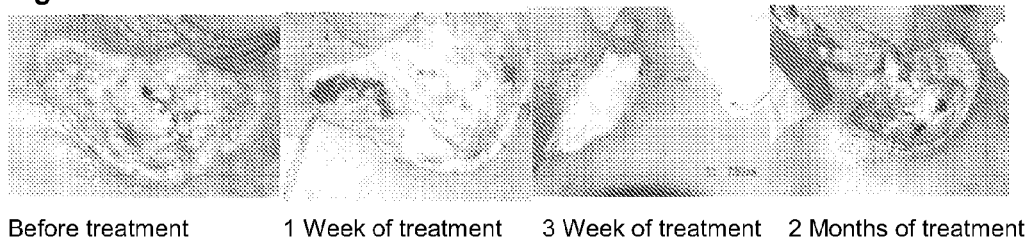
Before treatment     1 Week of treatment     3 Week of treatment     2 Months of treatment
Figure #8
Before treatment     After 4 phormulation Applications     End of treatment
Figure #9
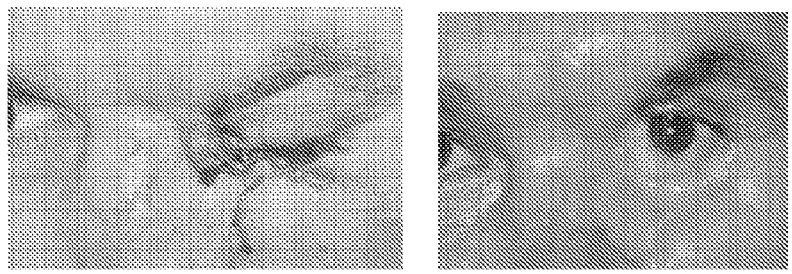
Before treatment     1 year after treatment

STABILIZED PHARMACEUTICAL FORMULATIONS THAT CONTAIN THE INTERFERONS GAMMAS AND ALPHA IN SYNERGISTIC PROPORTIONS This application is the U.S. National Phase of, and Applicants claim priority from, International Application Number PCT/CU2006/000011 filed 27 Oct. 2006 and Cuban Application bearing Serial No. CU-2005-0213 filed 2 Nov. 2005, which are incorporated herein by reference.

FIELD OF THE TECHNIQUE

The present invention relates to the biotechnology and the medical sciences, particularly with stabilized pharmaceutical formulations that contain the recombinants interferons gamma and alpha in synergistic proportions for the inhibition of the cell growth in different tissue or organs of the human beings.

STATE OF THE PREVIOUS TECHNIQUE

The variety of effects of the interferons type I (in English "Interferons", shortened IFNs) creates a great therapeutic potential of their applications. The IFNs application is beneficial in the treatment of various types of cancer, among them are included leukemias (U.S. Pat. No. 5,830,455), basal cell carcinoma (U.S. Pat. No. 5,028,422), squamous cell carcinoma (U.S. Pat. No. 5,256,410), breast cancer (U.S. Pat. No. 5,024,833), gastrointestinal tumors (U.S. Pat. No. 5,444,064; U.S. Pat. No. 5,814,640), and actinic keratosis (U.S. Pat. No. 5,002,764). Different cell types show a differential sensibility to the IFNs, and the concentrations to inhibit their growth can vary in an extensive rank (Borden E., et al. (1981) Progress in Hematology. vol XII, Brown E B., editor, 299-339), for which show differences in their capacity to inhibit the cell growth (Dahl H. (1983). Human interferon and cell growth inhibition. VII. Reversibility of interferon activities. J Interferon Animal, 3:327-332; Willson J. K. V., Bittner G., et al. (1984) Antiproliferative activity of human interferons against ovarian cancer cells grown in human tumor stem cell assay. J Interferon Animal, 4:441-447; Hu R., Gan Y., et al. (1993) Evidence for multiple binding sites for several components of human lymphoblastoid interferon-alpha. J Biol Chem, 268: 12591-12595), and to the activity antitumoral (Quesada J R., Talpaz M., et al. (1986) Clinical toxicity of interferons in cancer patients: to review. J Clin Oncol, 4:234-243). The use of the IFNs in the cancer therapy has not satisfied the expectations from the in vitro studies and the properties of these powerful biological molecules possess. Different therapeutic schedules have been tested without clear beneficial effects and impact (Strander H., and Oberg K., (1992) Clinical use of interferons. Solid tumors INTERFERON. Principles and Medical Applications. Publishing Baron S., Coppenhaver D H., Dianzani F., Fleischmann W R., Jr. Hughes T K., Jr. Klimpel G R., Niesel D W., Staton G J., and Tyring S K., 533-561).

In an effort to reach better effects in the therapies, the IFNs were employed at high doses, but the beneficial potential expected response does not appear, owed to various factors, among them the adverse reactions that are produced with said doses (Lane H. C. (1990) Interferon-alpha in patients with asymptomatic human immunodeficiency virus (HIV) infection. A randomized, placebo-controlled trial. Annals of internal Medicate, 112:805-811).

In addition, the IFNs have been used in combined form exploiting their synergistic effects. The combination of IFN alpha and IFN gamma has been described in in vitro studies with cultures from keloids fibroblast (Tredget E E., Wang R., et al. (2000) Transforming growth factor-beta mRNA and protein in hypertrophic scar tissues and fibroblasts: antagonism by IFN-alpha and IFN-gamma in vitro and in vivo. J Interferon Cytokine Animal, 20:143-151). In this work, the combined utilization of the IFNs alpha and gamma is mentioned, but the resulted data come from in vitro and in cells originating from keloids from children. These authors did not carry out any clinical trial and did not evaluate the effect of the IFNs combination on cells of adults keloids that are poor responder to the interferons.

The patent EP 0107498 shows the combination of the interferons alpha and gamma in the cell line of melanoma Hs294T, but dose not describe this effect in other types of cells like primary culture of basal cell carcinoma, or of a glioblastoma (GL-5), or of a laryngeal carcinoma (HEp-2).

The alternated utilization of natural IFN alpha and recombinant IFN gamma has also been described for the treatment of renal and lung metastasis (Fujii A., Yui-In K., et al. (1999) Preliminary results of the alternating administration of natural interferon-alpha and recombinant interferon-gamma for metastasic renal cell carcinoma BJU Int.; 84:399-404). The combination of IFN alpha 2, or alpha 4 or the hybrid delta 4 alpha 2 Bgl II alpha 1 with IFN gamma was described in the cell lines RT4 (bladder carcinoma) and in A2182 (lung adenocarcinoma), and possesses a superior antiproliferative effect than IFNs type I or IFN gamma alone, (Hubbell H. R., Craft J. TO., et al. (1987) Synergistic antiproliferative effect of recombinant alpha-interferons with recombinant gamma-interferon. J Biol Response Mod, 6:141-153). A synergistic effect among the IFN gamma (1000 IU/mL) and the IFN alpha 2 (1000 IU/mL) was shown in the cell line A459 (alveolar tumor), (Martyre M. C., Beaupain R., et al. (1987) Potentiation of antiproliferative activity by mix of human recombinant IFN-alpha 2 and -gamma on growth of human cancer nodules maintained in continuous organotypic culture. Eur J Cancer Clin Oncol, 23:917-920), as well as in cell lines established from non-small cell lung anaplastic carcinoma (Hand A., Pelin K., et al. (1993) Interferon-alpha and interferon-gamma combined with chemotherapy: in vitro sensitivity studies in non-small cell lung-cancer cell lines. Anticancer Drugs, 4:365-368).

The combination of IFN alpha and IFN gamma has been described in studies with the cell line HepG2, (Mizukoshi E., Kaneko S., et al. (1999) Up-regulation of type I interferon receptor by IFN-gamma. J Interferon Cytokine Animal, 19:1019-1023) and in the cell line AVA5 (Okuse C., Rinaudo J. A., et al. (2005) Enhancement of antiviral activity against hepatitis C virus in vitro by interferon combination therapy. Antiviral Animal, 65:23-34). These authors do not determine the antiproliferative effect, neither the more effective proportions in the combination of the alpha and gamma interferons in the cell line HepG2. In addition, the synergistic effect has been explored for TNF alpha and IFN gamma in the cell line Hepa1-6, a murine hepatoma (Sasagawa T., Hlaing M., et al. (2000) Synergistic induction of apoptosis in murine hepatoma Hepa1-6 cells by IFN-GAMMA and TNF-alpha. Biochem Biophys Common Animal, 272:674-680).

In the U.S. Pat. No. 5,190,751 the inhibition of the growth of leukemias cell lines of type B and of type T by the combination of IFN alpha and gamma is described. In none of the T cell lines evaluated, the potentiation of the growth inhibitory effect was observed, and in certain experimental conditions, the effects of the combinations were antagonistic. In the patent EP 010749 and in a publication (Czarniecki C. W., Fennie C. W., et al. (1984) Synergistic antiviral and antiproliferative activities of *Escherichia coli*-derived human alpha, beta, and gamma interferons. J Virol. 49:490-496), is shown also that the combination of the IFNs alpha and gamma not always is synergic and can be antagonistic. The efficacy of the combinations in a very extensive rank is mentioned, but it is not shown.

These data indicates that the employment of combinations of IFN alpha and gamma should be evaluated for an experimental definition which permit to identify what condition is the favorable one to establish an optimum combination for the treatment of an inadequate cell growth in a given tissues or organs. For such reason, to support a therapy and adequate dose these should be evaluated in experiments in vitro and in controlled clinical trials.

In a study with cell lines of Gliomas, the IFN gamma affected the characteristics of malignancy such as the proliferation and the migration of the studied tumor cells (Knupfer M. M., Knupfer H., et al. (2001) Interferon-gamma inhibits growth and migration of A172 human glioblastoma cells. Anticancer Animal, 21:3989-3994). Other wise, negative results with the employment of IFN gamma to treat the gliomas have been reported (Mahaley M. S., Bertsch L., Jr. et al. (1988) Systemic gamma-interferon therapy for recurrent gliomas. J Neurosurg, 69:826-829). The simultaneous employment of IFN gamma and IFN beta has turned out to be efficient in the inhibition of the growth of the cell line GBM-18, a multidrug resistant astrocitoma (Reddy P. G., et al. (1991) Systemic gamma-interferon therapy for recurrent gliomas. J Natl Cancer Inst, 83:1307-1315). Besides, it has been described, the combination of IFN gamma with alpha-difluoromethylornitine (DFMO) for the treatment of these tumors (U.S. Pat. No. 4,499,072). The U.S. Pat. No. 5,002,879, describes a similar therapy utilizing DFMO next to killer cells activated by lymphokines and IL-2. With respect to IFN alpha, its combination with other drugs has had not favorable effects in the treatment of the gliomas, and has shown toxicity (Buckner J. C., Burch P. A., et al (1998) Phase II trial of recombinant interferon-alpha-2a and eflornithine in patients with recurrent glioma. J Neurooncol. 36:65-70; Chang S. M., Barker F. G., et al. (1998) High dose oral tamoxifen and subcutaneous interferon alpha-2a for recurrent glioma. J Neurooncol, 37:169-176). Then, the treatment of this type of tumor can be favored for the combined use of the IFN alpha and the IFN gamma, on the base of an adequate selection of the proportions of its combination based on in vitro experiments and in clinical trials.

The larynx is the second more frequent place of cancer of the upper aero-digestive tract after the oral cavity. The laryngeal carcinoma is the most frequent tumor of head and neck and the most common cancer of larynx is the squamous cell carcinoma of (95% of all the cases). The survival in the cases of laryngeal tumors T3 and T4 is only 5 years in approximately the 30% of the patients submitted to laryngectomia (Djordjevic V., Milovanovic J., et al. (2004) Radical surgery of the malignant laryngeal tumors. Minutes Chir Lugosl, 51:31-35). It has been shown that the radiation therapy and the chemotherapy are not effective for the treatment of this carcinoma (Chen W., Guo X., et al. (2004) Long-term follow-up observation of clinical therapy for laryngeal carcinoma recurrence and cervical metastasis Lin Chuang Er Bi Yan Hou Ke Za Zhi. 18:536-537).

Nevertheless, the polychemotherapy together with the employment of IFN alpha has turned out beneficial in the treatment of the laryngeal cancer (Mantz C. A., Vokes E. E., (2001) Sequential induction chemotherapy and concomitant chemoradiotherapy in the management of locoregionally advanced laryngeal cancer Ann Oncol, 12:343-347). The combination of IL-2 and IFN alpha was evaluated in a phase II trial as therapy for the laryngeal carcinoma, but the results were not satisfactory (Clayman G. L., Young G., et al. (1992) Detection of regulatory factors of lymphokine-activated killer cell activity in head and neck cancer patients treated with interleukin-2 and interferon alpha. Ann Otol Rhinol Laryngol, 101:909-915). Few advances exist in the therapeutic of the laryngeal tumors. The combined use of the IFNs alpha and gamma would be able to contribute to improve the existing therapies to fight this type of tumors.

The U.S. Pat. No. 5,503,828 describes a composition of interferons characterized by containing at less 50% of the alleles of IFN alpha 2 and IFN alpha 8 and one or more additional species of IFNs of a group formed by IFN alpha 4, alpha 7, alpha 10, alpha 16, alpha 17, and alpha 21. While, the U.S. Pat. No. 4,503,035 shows a preparation of some species of IFN alpha, but that does not include alpha 1, alpha 5, alpha 14, and al IFN omega. These patents do not describe a formulation formed by the combination of recombinants IFN gamma and IFN alpha 2.

The U.S. Pat. No. 5,762,923 details an interferon liquid composition diluted in water with a not ionic detergent and benzilic alcohol in sufficient quantities to stabilize the IFN alpha that contains besides, an acid buffer. On the other hand, the U.S. Pat. No. 4,847,079 describes a pharmaceutical composition of interferon and timerosal, while the U.S. Pat. No. 4,675,184 shows an interferon formulation with polyhydric alcohol and an organic buffer as stabilizer and a conventional carrier or diluents of pH 3-6. The composition can have additionally an anionic surfactant and/or albumin as stabilizer. In the U.S. Pat. No. 5,236,707 and U.S. Pat. No. 5,431,909 are described amines as stabilizers (aliphatic primary amines) and organic sales of lithium, that protect the interferon from degradation and stabilize it.

The U.S. Pat. No. 4,496,537 refers liquids stable formulations of interferon-alpha that include human serum albumin composition, and alanine or glicine, water and a buffer system capable to maintain the pH between 6.5 and 8.0.

The U.S. Pat. No. 5,935,566 describes stable formulations of interferon-alpha that include in their composition a buffer system capable to maintain the pH in the rank from 4.5 to 7.1, polysorbate 80 as stabilizer, EDTA as chelating agent, sodium chloride as isotonozing agent, and m-cresol as antimicrobial preserving.

The U.S. Pat. No. 0,170,207 describes stable formulations of interferon-alpha that include in their composition a buffer system capable to maintain the pH in the rank from 4.5 to 9.0, a stabilizing agent, a not ionic surfactant and a regulator of the osmotic pressure.

In the request WO 89/04177 liquids pharmaceutical formulations of interferon-gamma are described that contains a buffer solution that maintains the pH in the rank from 4.0 to 6.0, a polyhydroxyl sugar as stabilizer and a not ionic detergent. The U.S. Pat. No. 4,895,716 refers compositions and methods for the stabilization of the interferon-gamma with lactobionic acid in a buffer glicine/acetate solution.

The U.S. Pat. No. 5,676,942 describes pharmaceutical compositions formed by subtypes of interferons of the type I obtained from natural sources, but not combined with the interferon gamma and do not define the proportions of those combinations, only describes those combinations for viral infections and not for the treatment of tumors. In none of the reports described previously has been utilized, characterized or mentioned a pharmaceutical formulation that contain the recombinant IFNs gamma and alpha 2 together in synergistic combinations. Potentialities in the combined utilization exist for IFN gamma and IFNs type I when they are mixed in definite proportions for the treatment of the cell growth of different degree of resistance to the therapies established and/or their combinations.

Keeping in mind these premises, it is necessary the development of stable pharmaceutical formulations that contain these IFNs in proportions that permit their safe, efficient, simple, and extensive employment, in individuals with benign or malignant tissue formations. This will permit a more optimum management of the combinations and does more viable the employment in the therapeutic of patients tributary of these treatments.

EXPLANATION OF THE INVENTION

The present invention resolves the problem before mentioned, providing stable pharmaceutical formulations to be applied by parenteral (liquids or freeze-dried), or topic way (gel, ungent or cream). They contain different quantities of the recombinant interferons gamma and alpha in synergistic proportions for the treatment of pathological events that contemplate not physiological benign or malignant growth of tissue or organs and that contain besides, excipients or vehicles pharmaceutically acceptable.

These formulations are the result of the in vitro assays with cell lines of different sensibility to IFNs and of clinical trials in different tumor entities, as well as of the evaluation of biological and physical-chemical stability of the recombinant IFNs gamma and alpha 2 in the presence of the different excipients or vehicles pharmaceutically acceptable.

The freeze-dried stable pharmaceutical formulations are composed of the recombinant IFN gamma and alpha 2 mixed in a buffer solution capable to maintain the pH between 4.9 and 7.5, which can be the ammonium or sodium acetate, the sodium succinate, sodium and/or potassium phosphate or the sodium citrate/phosphate.

These formulations also are composed of at least of a component selected from not reducing sugar compounds, amino acids, surfactants and stabilizing polymers. The not reducing sugars can be the sucrose or trehalose the amino acids can be glycine, histidine or leucine; while as surfactants are described polysorbate 20 or the polysorbate 80 and like stabilizing polymer polyethylene glycol, dextran or hydroxyethyl starch.

A materialization of the invention defined that the buffer solution should be employed in a rank of concentration between 10 and 20 mM. The sucrose or trehalose, should be used between 5 and 100 mg/mL; glycine, histidine or leucine should be employed in a rank of concentration between 1 and 20 mg/mL. The polysorbate should be employed between 0, 01 and 1 mg/mL, while polyethylene glycol, dextran and hydroxyethjstarch, they are employed in a range of concentration between 5 and 50 mg/mL.

Several materializations of the invention describe freeze-dried stable pharmaceutical formulations that contain recombinant IFN gamma in a rank of concentration between $5.6 \times 10^8$ IU and $1.4 \times 10^8$ IU and recombinant IFN alpha 2 in a rank of concentration between $6.8 \times 10^8$ IU and $1.7 \times 10^8$ IU. Or recombinant IFN gamma in a rank of concentration between $2.0 \times 10^8$ IU and $0.5 \times 10^8$ IU and recombinant IFN alpha 2 in a rank of concentration between $12 \times 10^8$ IU and $3.0 \times 10^8$ IU. Or recombinant IFN gamma in a rank of concentration between $4.0 \times 10^8$ IU and $1.0 \times 10^8$ IU and recombinant IFN alpha 2 in a rank of concentration between $80 \times 10^8$ IU and $20 \times 10^8$ IU. The formulations contain additionally 0.0802 g of potassium di-hydrogen phosphate, 0.249 g di-hydrated di-sodium hydrogen-phosphate, 4 g of sucrose, 0.8 g of glycine, 0.03 g of Tween 20, 1 g of polyethylene glycol 6000, and water for injection sufficient quantity for 100 mL and for 0.5 mL, 1 mL, 5 mL and 10 mL in the respective equivalent proportions.

The definition to mix the recombinant IFN gamma and IFN alpha in a rank of defined combination was obtained after an isobologram analysis. The concentration of recombinant IFN gamma between $5.6 \times 10^8$ IU and $1.4 \times 10^8$ IU and recombinant IFN alpha 2 in a rank of concentration between $6.8 \times 10^8$ IU and $1.7 \times 10^8$ IU, in one of the freeze-dried stable pharmaceutical formulations, was reached from the analysis of the studies of the inhibition of the growth of the primary culture originating from keloids (Kel 5a, Kel 17a) and from the CBC III. After an isobologram analysis the combination of 100 IU/mL (10 ng/mL) for recombinant IFN gamma with 100 IU/mL (0.5 ng/mL) of recombinant IFN alpha 2b that reduce the cell growth in vitro in a 21%, 43% and 47%, respectively, was identified (to see examples 1, 2 and 3, FIG. 1, Table 1).

The mixture of recombinant IFN gamma in a rank of concentration between $2.0 \times 10^8$ IU and $0.5 \times 10^8$ IU and recombinant IFN alpha 2 in a rank of concentration between $12.0 \times 10^8$ IU and $3.0 \times 10^8$ IU for the formulation was defined utilizing a clinical trial and report of treated cases by compassion. The randomized, controlled, triple blind clinical trial, evaluated the efficacy of the intralesional (I. L.) treatment in patients with basal cell carcinoma utilizing the stable freeze-dried formulation defined above (to see example 7, tables 9, 10, 11, and 12).

In the report of treated cases by compassion, that also contributed to define these proportions, were treated patients with epidermoid carcinoma (patient 1) and a patient with multiple recurrent basal cell carcinomas, and with previous grafts (patient 2), (to see example 8 FIG. 5 to, b, c, d; patient 1, and FIG. 6 to, b, c; patient 2, respectively).

The formulation that contains recombinant IFN gamma in a rank of concentration between $4.0 \times 10^8$ IU and $1.0 \times 10^8$ IU and recombinant IFN alpha 2 in a rank of concentration between $80 \times 10^8$ IU and $20 \times 10^8$ IU was defined with the analysis of the results from the study of the inhibition of the growth of glioblastoma (GL-5) cells by 50 IU/mL (5 ng/mL) of recombinant IFN gamma with 100 IU/mL (0.5 ng/mL) of recombinant IFN alpha 2b. In this way, an inhibition of the growth of the 55% is reached (example 3). In addition, it was taken into account the analysis of the study with the cell line HEp-2. In this case, the quantities of IFNs are of 5 IU/mL (0.5 ng/mL) of recombinant IFN gamma with 75 IU/mL (0.375 ng/mL) of recombinant IFN alpha 2b. With that, optimum combination is reached to reduce the cell growth in vitro in a 76% (to see examples 1, 2 and 3).

In addition were developed pharmaceutical stable liquid formulations. In these formulations the proportions of the recombinant IFNs gamma and alpha, were maintained as described for the freeze-dried formulations, but their pharmaceutical ingredients varied to achieve a greater stability to these mixtures of the IFNs.

As a consequence of this work a materialization of the invention describes liquid stable pharmaceutical formulations that contain a buffer solution and at least a component selected from non-reducing sugars, amino acids, surfactants, stabilizing polymers antioxidant/chelating components and isotonozing agents. These formulations employ a water based solvent that can contain or not preserving agents just as the mixture of methyl- and propyl-paraben.

Another materialization of the invention situates the definition of liquid stable pharmaceutical formulations that employ a buffer solution capable to maintain the pH between 4.9 and 6.5. This buffer can be ammonium or sodium acetate, sodium succinate, sodium and/or potassium phosphate, citrate/phosphate. These formulations can employ as surfactants polysorbate 20 or polysorbate 80; as antioxidant/chelating EDTA or acetyl cysteine; while as amino acids can include histidine, L-arginine, L-alanine, glycine or lysine. As stabilizing polymer is defined the utilization of the hydroxyethyl starch or dextran and as isotonozing agent sodium chloride, potassium chloride, propylene glycol, manitol, glycerol, sucrose or trehalose.

A materialization of the invention collects that the liquid stable pharmaceutical formulations employ a buffer solution in a rank of concentration between 10 and 100 mM. In this formulation the polysorbate is employed in a rank of concentration between 0, 01 and 1 mg/mL; the EDTA or the acetyl cysteine are employed in a rank of concentration between 0, 01 and 1 mg/mL. The amino acids histidine, L-arginine, L-alanine, glycine or lysine are at a concentration between 1 and 20 mg/mL; the hydroxyethyl starch and dextran are employed in a rank of concentration between 5 and 50 mg/mL and the isotonozing agents are found in sufficient quantity to make the solution isotonic.

Other materializations explain the quantities of all the pharmaceutical ingredients of the liquid stable pharmaceutical formulations necessary for the physico-chemical and biological stability of the mixtures of the recombinant IFNs gamma and alpha described previously. These liquid formulations contain besides the IFNs, 0.708 g of sodium acetate, 0.079 mL of acetic acid, 0.01 g of Tween 20, 5 g of manitol, and water for injection sufficient quantity for 100 mL and for 0.5 mL, 1 mL, 5 mL and 10 mL in the respective equivalent proportions.

This invention defines the proportions of mixtures of IFNs gamma and alpha that can be profitable for the treatment of the benign or malignant overgrowth of cells. This will permit to employ smaller dose, less time of treatment and to maintain the same therapeutic effects or to achieve effects over the ones that have been reached until today with the employment of the interferons in the treatment of the tumors or other aberrant events of cell growth. Lowering the dose will permit to expect less adverse effects or smaller intensity of them, that will give a better quality of life to the patients and will permit them to obtain the benefits of the use of these powerful drugs.

The invention defines formulations of the mixture of recombinant IFN gamma and IFN alpha 2 that have not been described previously, that facilitate the management and clinical use of this therapeutic combination and their commercialization.

The freeze-dried and liquid stable pharmaceutical formulations that contain mixtures of the recombinant IFNs gamma and alpha 2 in synergistic proportions for the inhibition of the proliferation described in the invention, has an extensive spectrum of clinical use. It is shown in vivo utilizing these formulations, that in important oncological diseases, the combination of the recombinant IFN gamma and the IFN alpha 2 is effective utilized simultaneous and intratumoral.

This combination is capable of having equals curative effects on tumors in shorter time and with a higher esthetic effect when compared with that obtained for its separated components. The use of these combinations will permit to include greater therapeutic possibilities to fight the cancer. This it is collected in a materialization of the invention where is exposed that the freeze-dried or liquid formulations can be employed in the treatment of solid benign or malignant tumors, utilized in independent forms or combined with chemotherapy, radiation therapy or the combination of both.

The utilization of these formulations in combination with other therapeutic agents is supported in the results obtained with the treatment of a patient with a giant basal cell tumor with the combination of recombinant IFN gamma and IFN alpha 2 along with cisplatin (to see example 10 and FIG. 9).

It is described in the invention how the combined employment of the interferons gamma and alpha 2 permits to reduce and/or to cure tumors of very badly forecast and of distorting esthetic effects.

According to the characteristics of several benign and oncological entities where predominates an uncontrolled growth of cells, they can be susceptible to be treated with these formulations. Among them are: Tumors of the cells from hematopoyetic tissue such as the acute or chronic myeloid leukemia, acute or chronic lymphocytic leukemia, as well as the leukemias of T, or B cells and the lymphoma of the central nervous system. Can also be treated the laryngeal carcinomas, the laryngeal papilomatosis, the lypoma, the epidermoid and intradermic cyst, the lyposarcoma, the neurofibroma, and the sebaceous hyperplasia. Can be beneficed with the use of these pharmaceutical formulations tumors from peripheral and central nervous system as the astrocitomas, multiform glioblastomas, ependimomas, ganglioneuromas, pilocitic astrocitomas, mixed gliomas, oligodendrogliomas, gliomas of the optic nerve, primitive neuroectodermal tumors, acoustic neuromas, cordomas, craniofaringiomas, meduloblastomas, meningiomas, neurofibromatosis, pseudotumors of brain, tuberose sclerosis, metastasic cerebral tumors. Other susceptible tumors to be treated are the cavernous hemangiomas, hepatocellular adenomas, focal hyperplasia nodular, pineal tumors, pituitary adenomas, vascular tumors, meningeal carcinomatosis, cherry like angiomas, sebaceous gland hyperplasia. The tumors of skin as the basal cell carcinoma, squamous cells carcinoma, the dermatofibroma, the piogenic granuloma, skin nevus, as well as seborreic and actinic queratosis can be beneficed from the therapy with these pharmaceutical formulations.

Another materialization of the invention describes that these formulations can also be employed for the treatment of proliferative events as fibrosis, dysplasia and hyperplasia.

According to the results of the clinical trials carried out and described in the examples 7, 8, and 10 as materialization of the invention are defined the intramuscular, intratumoral, and perilesional ways of application of the formulations. Other materializations describe the application of topic stable pharmaceutical formulations that contain IFN gamma in a rank of concentration between $0.32 \times 10^6$ IU and $0.08 \times 10^6$ IU and al IFN alpha 2 in a rank of concentration between $2.0 \times 10^6$ IU and $0.5 \times 10^6$ IU by gram of semisolid. The formulations are cream composed by 2.2% IFN gamma, 0.58% IFN alpha, 4% of celtilic alcohol, 10% vaseline, 2% Tween 60, and 0.2% methylparaben, propylparaben. In addition, the composition of unguent was defined by 2.2% IFN gamma 0.58% IFN alpha, 60% of white solid petrolate, 10% of heavy liquid petrolate, 3% of span 20, and 0.2% methylparaben and propylparaben. Finally, the gel formulation is composed by 2.2% IFN gamma, 0.58% IFN alpha, 0.5% of Carbopol 940, 0.2% of methylparaben and propylparaben, 0.2% of sodium hydroxide, 0.01% of calcium di-sodium ethylenediaminotetracetate and 2% ethanol.

All these formulations are resistant to the fluctuations of temperature, which is profitable for the production of the product, its transportation and storage. They prevent the aggregation of the interferons and therefore they present smaller risk to result immunogenic during the use prolonging of the product. The formulations of semisolid permit the employment by the own patients by not invasive and safe form. As another materialization of the invention was defined the employment of these topic stable formulations in the treatment of solid benign or malignant tumors of the skin or mucous membranes, utilized in independent forms or combined with chemotherapy, radiation therapy or the combination of both.

Another materialization of the invention describes that, the topic stable pharmaceutical formulations can be employed for the treatment of lypoma, epidermoid and intradermic cyst, lyposarcoma, neurofibroma, sebaceous hyperplasia, hemangiomas, focal nodular hyperplasia, ependimomas, ganglioneuromas, pilocitic astrocitomas, meningiomas, pienal tumors, pituitary adenomas, vascular tumors, meningeal carcinomatosis, neurofibromatosis, cherry like angiomas, hyperplasia of the sebaceous glands, basal cell carcinoma, squanous cell carcinoma, dermatofibroma, piogenic granuloma, skin nevous, seborreic and actinic queratosis, and condilomas.

Another materialization of the invention described the conformation of a kit that contains a vial of recombinant IFN gamma, a vial of recombinant IFN alpha to the concentrations and relations described previously, with a sufficient quantity of water for injection vials, for the dilution and/or dissolution of the IFNs. The kit contains the syringes and adequate needles for the simultaneous administration of the IFNs, previously mixed in one of the vials that contain one of the IFNs.

BRIEF DESCRIPTION OF THE FIGURES

FIG. 1. Growth inhibition of fibroblast primary cell culture originating from biopsies of adult patients with keloids by 1000 IU/mL of recombinant IFN gamma or IFN alpha 2.

FIG. 2. Isobologram of the cell growth inhibition by the combination of recombinant IFN gamma and IFN alpha 2b on fibroblasts primary cell culture from keloid (Kel5a).

FIG. 3. Isobologram of the cell growth inhibition by the combination of recombinant IFN gamma and IFN alpha 2b on fibroblasts primary cell culture from keloid (Kel17a).

FIG. 4. Isobologram of the cell growth inhibition by the combination of recombinant IFN gamma and IFN alpha 2b on fibroblasts primary cell culture from basal cell carcinoma (CBC III).

FIG. 5. Isobologram of the cell growth inhibition by the combination of recombinant IFN gamma and IFN alpha 2b on the cell line of the glioblastoma GL-5.

FIG. 6. Isobologram of the cell growth inhibition by the combination of recombinant IFN gamma and IFN alpha 2b on the cell line from laryngeal HEp-2.

FIG. 7. Patient with epidermoid carcinoma treated with the combination of recombinant IFN gamma and IFN alpha 2b.

FIG. 8. Patient with recurrent basal cell carcinoma treated with the combination of recombinant IFN gamma and IFN alpha 2b.

FIG. 9. Patient with recurrent basal cell carcinoma treated with the combination of recombinant IFN gamma and IFN alpha 2b and cisplatin. A: before treatment, B: after 1 year of treatment.

DETAILED EXPOSITION OF WAYS OF EXECUTION

Examples

Example 1

Inhibition of the Cell Growth by the Recombinant IFNs Gamma or Alpha on Primary Cell Culture The skin biopsies were obtained from normal skin and from patients that developed basal cell carcinoma or keloids, the last due to damage by surgery or burns. The tissue sample was placed immediately in medium DMEM and fragmented to obtain primary culture by explant method. For the evaluation of the antiproliferative effect of the recombinant IFNs gamma and alpha the following primary culture were evaluated: Fibroblast primary culture (CPF) from keloids (1, 2, 5, 7, 8, 15, 17, 19, 20, 24, 26, 27, 31, 32), CPF from basal cell carcinoma (CBC III) and CPF from normal skin (FibN3 and FibN5). The CPF were growth in a culture media mixture RPMI-1640/DMEM that contained gentamicine (50 µg/ml), and 12% of calf bovine serum (CBS). All the cultures were incubated at 37° C. in a $CO_2$ incubator with 5% humidity. To determine the antiproliferative effect of the IFNs, the cells were seeded at $5 \times 10^4$ cells/mL in 96 microwell plates. They were synchronized by changing of fresh medium after 24 hours after seeding. At the end of 96 hours of incubation in the presence of different concentrations of the IFNs was determined the viability of 3 replicas of evaluated experimental conditions utilizing the method crystal violet staining, measuring the absorbance at 580 nm and utilizing a reader plates. The results were defined as the % of growth based on the count of viable cells:

$$\% \text{ of growth} = (AT_{72h} - AC_{0h}/AC_{72h} - AC_{0h}) \times 100.$$

$AT_{72h}$=Absorbance of cell treated 72 h.
$AC_{72h}$=Absorbance of control cells treated 72 h.
$AC_{0h}$=Absorbance of cell before been treated with IFN.

In the FIG. 1 is shown the antiproliferative action of the recombinant IFNs gamma or alpha on the growth of the keloids CPF. As it can be observed the IFN gamma or alpha 2b inhibits the cell proliferation in various primary culture, while in other they stimulate their growth. As controls were evaluated the primary culture FibN3 and FibN5, as well as primary culture from biopsy of a CBCIII, and HEp-2, U1752 and GL-5 cell lines.

Example 2

Inhibition of the Cell Growth by the Recombinant IFNs Gamma or Alpha Recombinantes on Established Cell Lines The human cell lines studied were: Jurkat (ATCC, TIB-152), GL-5 (Perea S, and, et al. (1993) Minutes Cient Venez, 44:22-27), HEp-2 (ATCC, CCL23). The cells GL-5 were cultured in DMEM, and the HEp-2 in MEM-CANE containing gentamicine (50 µg/ml) and 10% CBS. The Jurkat cells were incubated in the RPMI medium with gentamicine and 10% CBS. All the culture were incubated at 37° C. in a $CO_2$ incubator of with 5% of humidity. To evaluate the antiproliferative effect on GL-5 and HEp-2 cells were seeded at $3 \times 10^4$ cells/mL. In the case of the Jurkat cells, these were seeded to $10^5$ cells/mL. After 72 hours of incubation in the presence of different concentrations of the IFNs the viability of 3 replicas were evaluated, utilizing the method of violet crystal staining, and measuring the absorbance at 580 nm and utilizing a reader plates. The results were defined as the % of growth based on the count of viable cells as described in the example 1. As it is observed in the table 1 and in the FIG. 1, the cell lines HEp-2 (laryngeal carcinoma) and the GL-5 (from a glioblastoma), are very sensitive to IFN gamma and not to IFN alpha.

TABLE 1

Inhibition of the cell growth by 1000 IU/mL of IFN gamma or IFN alpha 2b on cell lines.

| IFNs | Average | Standard deviation SD | Variation Coefficient CV | Replicates | Assays |
|---|---|---|---|---|---|
| HEp-2 | | | | | |
| IFN Alpha 2 | 65% | 13.68% | 0.211 | 6 | 2 |
| IFN gamma | 18% | 6.26% | 0.357 | 6 | 2 |
| GL-5 | | | | | |
| IFN Alpha 2 | 71% | 20.26% | 0.287 | 6 | 2 |
| IFN gamma | 24% | 10.21% | 0.421 | 4 | 2 |
| HepG2 | | | | | |
| IFN Alpha 2 | 103% | 13.17% | 0.128 | 6 | 1 |
| IFN gamma | 106% | 21.67% | 0.204 | 6 | 1 |
| Jurkat | | | | | |
| IFN Alpha 2 | 60% | 5.28% | 0.088 | 3 | 1 |
| IFN gamma | 107% | 16.89% | 0.157 | 3 | 1 |

In the Table 1 is observed that the line HepG2 (Hepatoma) is not sensitive to these IFNs and that in the cell line Jurkat (lymphoma T), the IFN alpha is the most effective one, result that coincides with the successful employment of the IFN alpha 2 in the treatment of tumor from lymphoid tissue.

Example 3

Combinations of the Recombinant IFNs Gamma and Alpha with More Effective Antiproliferativa Action on the Primary Culture and Cell Lines Utilizing the CBC-III and keloids (Kel-5a and Kel-17a) CPF and the cell lines HEp-2 and GL-5, studies of combinations were carried out with recombinant IFNs gamma and alpha 2b, to define optimum mixture with synergistic activity of the inhibition of the cell growth. The data obtained in the studies were analyzed building isobolograms. From the isobolograms studies of CPF originating from biopsies of adult keloids (kel 5a and kel 17a) was defined that the optimum synergistic combination for the inhibition of the growth should be composed of 100 IU/mL (10 ng/mL) of IFN gamma and 100 IU/mL (0.5 ng/mL) of IFN alpha 2b. With that combination the cell growth is reduced in vitro in a 21% (Kel 5a) and in a 43% (kel 17a) (FIGS. 2 and 3).

In the isobologram of the FIG. 4 is shown that the combination of 100 IU/mL (10 ng/mL) of IFN gamma with 100 IU/mL (0.5 ng/mL) of IFN alpha 2b is synergistic and is the most efficient in reducing the in vitro cell growth of the CBC III in a 47%. According to the isobologram that is shown in the FIG. 5, the optimum synergistic combination to inhibit the growth of the cells of the GL-5 is 50 IU/mL (3 ng/mL) of IFN gamma with 600 IU/mL (5 ng/mL) of IFN alpha 2b. With that combination, the in vitro cell growth is reduced in a 55%.

In the isobologram represented in the FIG. 6 is shown the optimum synergistic combination of IFN gamma and alpha to obtain the best antiproliferative effect on the HEp-2 cells. The quantities of IFNs are of 5 IU/mL (0.5 ng/mL) of IFN gamma with 75 IU/mL (0.375 ng/mL) of IFN alpha 2b. With that optimum combination is reached a reduction the cell growth in vitro in a 76%.

Example 4

Effect of the pH, the Ionic Species and the Concentration of the Buffer Solution in the Stability of the Mixture of the Interferons Alpha-2b and Gamma in Water Solution To study the stability of the liquids and freeze-dried formulations of the synergistic compositions of the recombinant interferons gamma and alpha, the IFNs were diluted from their corresponding Active Pharmaceutical Ingredient (IFA) in different assay formulations: buffer solutions, buffer solutions mixture with individual excipients and buffer solutions mixture with various excipients. Representative samples of the vials of the different formulations were submitted to different treatment to evaluate the stability of the interferons: Cycles of freezing-thawing, lyophilization, agitation to 37° C., effect of the light and of the temperature. After the different processing, the physical-chemical stability was evaluated through different assays: physical appearance, sodium dodecilosulphate polyacrylamide gel electrophoresis (SDS-PAGE), reverse-phase liquid chromatography (RP-HPLC) and chromatography of molecular exclusion (ME-HPLC). The biological stability was evaluated by immuno-enzymatic assays (ELISA) specific for each interferon and by biological assays of inhibition of the viral cytophatogenic effect.

All these formulation design studies were carried out with the mixture of intermediate concentrations of the interferons (0.5 MIU of IFN gamma and 3.0 MIU of IFN alpha 2b). With the final variants of formulation obtained (prepared by duplicate) the synergistic compositions were prepared and its stability evaluated.

Organoleptic Characteristic:

It was determined by the analysis of the appearance of the formulation (if was maintained colorless, transparent and without aggregation of proteins). In the freeze-dried formulation, also the appearance of the freeze-dried product was analyzed.

The Humidity:

The content of residual humidity of the freeze-dried product was determined by the technique of Karl Fischer yodometric titration, employing a meter of humidity Radiometer (Model TIM 550).

Chemical Stability:

The purity of the proteins and the magnitude of the degradation was determined by RP-HPLC in a column C8 Vydac equipped with a keeping-column C8 Vydac (Vydac, Hesperia, Calif.) using a HPLC system Merck-Hitachi equipped with a system of solvent liberation, a diode arrangement detector, an oven and a data processing system. The purity of the proteins also was determined by SDS-PAGE.

Aggregates Determination:

The aggregation of the recombinant IFN gamma and of the IFN alpha 2b was measured by molecular exclusion HPLC using a Superdex-75 HR 10/30 column (Amersham Pharmacia Biotech AB, Sweden) and a HPLC system Merck-Hitachi equipped with a solvent liberation system, a diode arrangement detector, an oven and a data processing system. The content of covalent aggregates was determined by SDS-PAGE.

Alpha Interferon ELISA:

This assay has been developed in our laboratory (H. Santana., Espino Y., et al. (1999) A sandwich-type enzyme-linked immunosorbent assay for the analysis of recombinant human interferon α-2b. Biotechnology Techniques, 13, 341-346). The assay employs monoclonal antibodies and was carried out following the reported methodology. The measurement is reported here as percentage of the residual ELISA activity of the interferon alfa-2b in the different samples from each formulation variants, taking the ELISA activity in the initial sample as 100%.

Interferon Gamma ELISA:

This assay has been developed in our laboratory (Bouyón R., Santana H., et al. (2003) Development and validation of an enzyme-linked immunosorbent assay (ELISA) for recombinant human gamma interferon. *Journal of Immunoassay and Immunochemistry*, 24:1-10). The assay employs monoclonal antibodies and was carried out following the reported methodology. The measurement is reported here as percentage of the residual ELISA activity of the interferon gamma in the different samples from each formulation variants, taking the activity ELISA in the initial sample as 100%.

Antiviral Biological Activity Quantification:

The measurement of the biological activity was carried out as described Ferrero J., Ochagavia M E., et al. (1994, Titulación de la actividad antiviral del interferón utilizando el sistema de equipos SUMA. *Biotecnologia Aplicada*, 11:34-42). The calculation of the biological activity was carried out as describes Ferrero J., Duany L., et al. (1997, Nuevo programa de cálculo, cuantificación de la actividad antiviral de interferones mediante la inhibición del efecto citopatogénico utilizando el sistema de equipos SUMA. *Biotecnologia Aplicada*, 14: 267-269). The biological activity is reported here as percentage of the residual biological activity, taking the biological activity of the initial sample as 100%. To know the effect of the pH in the stability of the active ingredients, different formulations containing 0.5 MIU of IFN gamma and 3.0 MIU of IFN alpha 2b in different buffer solutions were prepared; that is to say, buffer citrate/phosphate, buffer phosphate, buffer citrate and buffer acetate. The formulations containing the mixtures of recombinant IFN gamma and of IFN alpha 2b with the buffer solutions and submitted to cycles of freezing-thawing or stored at 45° C. and analyzed by ELISA at different time intervals. The formulations were prepared as to have the pH between 4 and 8, and all the buffer solutions at a concentration of 0.1 M. The tables 2, 3 and 4 reported the results of the assays carried out after 3 cycles of freezing-thawing and at different intervals of time, from 3 to 12 days at of 45° C.

TABLE 2

Stability at 45° C. and during freezing-thawing cycles of recombinant IFN gamma and IFN alpha 2b mixture (0.5 MIU IFN gamma and 3.0 MIU IFN alpha 2b) in water buffer solution citrate/phosphate 0.1 M at different pH. Concentration of IFN gamma and IFN alpha 2b in percentage (%).

| | FREEZING-THAWING | | INCUBATION AT 45° C. | | | | | |
|---|---|---|---|---|---|---|---|---|
| | ELISA | ELISA | ELISA IFNγ | | | ELISA IFNα | | |
| T = 0 | IFNγ | IFNα | 3 D | 6 D | 12 D | 3 D | 6 D | 12 D |
| IFN/4 100 2690650 IU/ML | 25.9 | 73.0 | 4.5 | ND | ND | 78.5 | 69.9 | 36.9 |
| IFN/5 100 3820902 IU/ML | 82.1 | 86.5 | 5.4 | ND | ND | 81.4 | 62.6 | 31.7 |
| IFN/6 100 3532107 IU/ML | 63.3 | 82.7 | 36.5 | 5.5 | 3.6 | 79.8 | 61.0 | 38.5 |
| IFN/7 100 3532100 IU/ML | 63.0 | 82.4 | 44.4 | 26.4 | 14.0 | 78.0 | 63.1 | 32.0 |
| IFN/8 100 3179500 IU/ML | 55.1 | 76.7 | 37.6 | 21.6 | 11.5 | 82.5 | 60.3 | 34.2 |

D = Days;
ND = not determinable.
IFN/4 = formulation in buffer citrate/phosphate pH 4.0;
IFN/5 = formulation in buffer citrate/phosphate pH 5.0;
IFN/6 = formulation in buffer citrate/phosphate pH 6.0;
IFN/7 = formulation in buffer citrate/phosphate pH 7.0;
IFN/8 = formulation in inkpad citrate/phosphate pH 8.0.

TABLE 3

Stability at 45° C. and during freezing-thawing cycles of recombinant IFN gamma and IFN alpha 2b mixture (0.5 MIU IFN gamma and 3.0 MIU IFN alpha 2b) in water buffer solution of phosphate 0.1 M at different pH. Concentration of IFN gamma and IFN alpha 2b in percentage (%).

| | FREEZING-THAWING | | INCUBATION AT 45° C. | | | | | |
|---|---|---|---|---|---|---|---|---|
| | ELISA | ELISA | ELISA IFNγ | | | ELISA IFNα | | |
| T = 0 | IFNγ | IFNα | 3 D | 6 D | 12 D | 3 D | 6 D | 12 D |
| IFN/5 100 3549425 IU/ML | 90.2 | 83.5 | 67.3 | 47.6 | 25.4 | 74.1 | 53.9 | 32.6 |
| IFN/6 100 3459600 IU/ML | 67.8 | 75.6 | 42.4 | 28.6 | 10.5 | 82.7 | 59.6 | 41.1 |
| IFN/7 100 3523210 IU/ML | 57.9 | 80.4 | 40.5 | 21.5 | 8.1 | 73.6 | 52.9 | 33.0 |
| IFN/8 100 3321090 IU/ML | 57.2 | 78.5 | 26.1 | 10.7 | 6.5 | 74.9 | 59.0 | 37.3 |

D = Days;
ND = not determinable.
IFN/5 = formulation in buffer phosphate pH 5.0;
IFN/6 = formulation in buffer phosphate pH 6.0;
IFN/7 = formulation in buffer phosphate pH 7.0;
IFN/8 = formulation in buffer phosphate pH 8.0

The data from these tables (2, 3, 4) indicate that the formulations with values of pH between 5 and 8 have an adequate stability during the freezing-thawing cycles, preferably for the pH close to 5 and to 7 and in the buffer acetate, phosphate and citrate-phosphate. The thermal stability in water solution was greater to values of pH between 5 and 5.6, preferably in the buffer acetate and phosphate.

The data from table 5 indicate that the formulations of higher buffer concentration showed better stability during the freezing-thawing cycles than those of lower concentration to pH 5.5, particularly for the IFN gamma in the different evaluated buffers. Nevertheless, the results of the thermal stability were better for pH 5.5 in the buffer acetate followed by phosphate. Dependence from the concentration was not observed. The thermal stability in buffer citrate-phosphate was better in buffer of low concentrations.

TABLE 4

Stability at 45° C. and during freezing-thawing cycles of recombinant IFN gamma and IFN alpha 2b mixture (0.5 MIU IFN gamma and 3.0 MIU IFN alpha 2b) in water buffer solution of citrate and acetate 0.1 M at different pH. Concentration of IFN gamma and IFN alpha 2b in percentage (%).

| | FREEZING-THAWING | | INCUBATION AT 45° C. | | | | | |
| | ELISA | ELISA | ELISA IFNγ | | | ELISA IFNα | | |
| T = 0 | IFNγ | IFNα | 3 D | 6 D | 12 D | 3 D | 6 D | 12 D |
|---|---|---|---|---|---|---|---|---|
| IFN/C4 100 2690650 IU/ML | 11.9 | 77.0 | 1.3 | ND | ND | 66.9 | 49.9 | 27.0 |
| IFN/C5 100 3820902 IU/ML | 64.6 | 78.1 | 2.7 | ND | ND | 71.3 | 56.6 | 41.8 |

TABLE 4-continued

Stability at 45° C. and during freezing-thawing cycles of recombinant IFN gamma and IFN alpha 2b mixture (0.5 MIU IFN gamma and 3.0 MIU IFN alpha 2b) in water buffer solution of citrate and acetate 0.1 M at different pH. Concentration of IFN gamma and IFN alpha 2b in percentage (%).

| | FREEZING-THAWING | | INCUBATION AT 45° C. | | | | | |
| | ELISA | ELISA | ELISA IFNγ | | | ELISA IFNα | | |
| T = 0 | IFNγ | IFNα | 3 D | 6 D | 12 D | 3 D | 6 D | 12 D |
|---|---|---|---|---|---|---|---|---|
| IFN/C6 100 3532107 IU/ML | 65.8 | 66.9 | 12.0 | 5.9 | ND | 61.5 | 43.7 | 28.2 |
| IFN/A4 100 3532100 IU/ML | 87.1 | 82.3 | 65.9 | 46.4 | 27.9 | 64.5 | 46.6 | 29.0 |
| IFN/A5 100 3179500 IU/ML | 86.1 | 79.7 | 59.4 | 45.9 | 24.0 | 68.3 | 47.9 | 30.7 |
| IFN/A5.6 100 3179500 IU/ML | 74.8 | 75.0 | 50.8 | 31.3 | 18.9 | 67.7 | 48.3 | 27.6 |

D = Days;
ND = not determinable;
IFN/C4 = formulation in buffer citrate pH 4.0;
IFN/C5 = formulation in buffer citrate pH 5.0;
IFN/C6 = formulation in buffer citrate H 6.0;
IFN/A4 = formulation in buffer acetate pH 4.0;
IFN/A5 = formulation in buffer acetate pH 5.0;
IFN/A5.6 = formulation in buffer acetate pH 5.6.

TABLE 5

Stability at 45° C. and during freezing-thawing cycles of recombinant IFN gamma and IFN alpha 2b mixture (0.5 MIU IFN gamma and 3.0 MIU IFN alpha 2b) in water solution pH 5.5 in buffer citrate-phosphate, phosphate and acetate at different concentrations. Concentration of IFN gamma and IFN alpha 2b in percentage (%).

| | FREEZING-THAWING | | INCUBATION AT 45° C. | | | | | |
| | | | ELISA IFNγ | | | ELISA IFNα | | |
| T = 0 | ELISA IFNγ | ELISA IFNα | 3 D | 6 D | 12 D | 3 D | 6 D | 12 D |
|---|---|---|---|---|---|---|---|---|
| IFN/C-F25 100 2690650 IU/ML | 59.2 | 77.2 | 62.8 | 21.7 | 27.9 | 67.2 | 59.9 | 38.7 |
| IFN/C-F50 100 3820902 IU/ML | 61.9 | 79.6 | 45.5 | 26.4 | 16.6 | 71.9 | 62.3 | 36.1 |
| IFN/C-F100 100 3532107 IU/ML | 63.3 | 82.7 | 36.5 | 5.5 | 3.6 | 79.8 | 61.0 | 38.5 |
| IFN/Fk25 100 3532100 IU/ML | 70.9 | 73.0 | 71.2 | 50.9 | 30.5 | 61.4 | 54.4 | 36.8 |
| IFN/Fk50 100 3179500 IU/ML | 79.7 | 75.9 | 69.1 | 48.7 | 28.7 | 63.6 | 52.9 | 31.6 |
| IFN/Fk100 100 3179500 IU/ML | 90.2 | 83.5 | 67.3 | 47.6 | 25.4 | 74.1 | 53.9 | 32.6 |
| IFN/FNa 25 100 3532100 IU/ML | 70.3 | 77.6 | 68.4 | 47.3 | 24.3 | 63.6 | 56.1 | 37.7 |
| IFN/FNa 50 100 3179500 IU/ML | 82.8 | 80.1 | 60.8 | 46.5 | 21.4 | 71.3 | 53.1 | 34.6 |
| IFN/FNa100 100 3179500 IU/ML | 87.9 | 86.5 | 73.9 | 42.0 | 32.5 | 74.7 | 52.9 | 35.0 |
| IFN/A25 100 3532100 IU/ML | 62.6 | 66.3 | 73.4 | 45.3 | 34.2 | 63.1 | 44.3 | 28.4 |
| IFN/A50 100 3179500 IU/ML | 69.3 | 69.0 | 67.3 | 42.9 | 29.7 | 65.6 | 51.9 | 33.2 |

TABLE 5-continued

Stability at 45° C. and during freezing-thawing cycles of recombinant IFN gamma and IFN alpha 2b mixture (0.5 MIU IFN gamma and 3.0 MIU IFN alpha 2b) in water solution pH 5.5 in buffer citrate-phosphate, phosphate and acetate at different concentrations. Concentration of IFN gamma and IFN alpha 2b in percentage (%).

|  | FREEZING-THAWING | | INCUBATION AT 45° C. | | | | | |
|---|---|---|---|---|---|---|---|---|
|  | | | ELISA IFNγ | | | ELISA IFNα | | |
| T = 0 | ELISA IFNγ | ELISA IFNα | 3 D | 6 D | 12 D | 3 D | 6 D | 12 D |
| IFN/A100 100 3179500 IU/ML | 76.4 | 77.1 | 52.6 | 30.1 | 22.8 | 70.5 | 49.0 | 26.8 |

D: Days;
ND: not determinable;
IFN/C-F25: formulation in buffer citrate-phosphate pH 5.5, 25 mM;
IFN/C-F50: formulation in buffer citrate-phosphate pH 5.5, 50 mM;
IFN/C-F100: formulation in buffer citrate-phosphate pH 5.5, 100 mM;
IFN/Fk25: formulation in buffer potassium-phosphate pH 5.5, 25 mM;
IFN/Fk50: formulation in buffer potassium-phosphate pH 5.5, 50 mM;
IFN/Fk100: formulation in buffer phosphate 5.5, 100 mM;
IFN/FNA 25: formulation in buffer sodium phosphate pH 5.5, 25 mM;
IFN/FNA 50: formulation in buffer sodium phosphate pH 5.5, 50 mM;
IFN/FNA 100: formulation in buffer sodium phosphate pH 5.5, 100 mM;
IFN/A 25: formulation in buffer acetate pH 5.5, 25 mM;
IFN/A 50: formulation in buffer acetate pH 5.5, 50 mM;
IFN/A 100: formulation in buffer acetate pH 5.5, 100 mM.

Example 5

Freeze-Dried Formulation ($1.4 \times 10^6$ IU of IFN Gamma and $1.7 \times 10^6$ IU of IFN Alpha 2b Per Vial)

Composition: IFN gamma $2.8 \times 10^8$ IU, IFN alpha 2b $3.4 \times 10^8$ IU, di-hydrogen potassium phosphate 0.0802 g, di-sodium di-hydrated hydrogen phosphate 0.249 g, sacharose 4 g, glicine 0.8 g, Tween 20 0.03 g, polyetilenglycol 6000 1 g, water for injection sufficient quantity for 100 mL.

All the components except the interferons were measured and diluted with water for injection. The pH of the solution is checked and if is necessary, adjusted to a value of 7.2±0.2 with diluted (1:2) acetic acid or with 1 M of NaOH. The active pharmaceutical ingredients of IFN gamma and IFN alpha 2b were added and diluted to the appropriate concentration. The solution was filtered in sterile form and the vials filled and capped with plugs for the lyophilization in a class 100 area, where the process was carried out. Finally, the vials are covered and sealed; and the product stored between 2 and 8° C. The table 6 shows the main parameters of the lyophilization cycle employed.

TABLE 6

Summary of the parameters of the lyophilization cycle.

| Cycle steps | Temperature | Duration |
|---|---|---|
| Freezing | −45° C. | 2 hours |
|  | −20° C. | 2 hours |
|  | −45° C. | 6 hours |
| Primary driying | −35° C. | 12 hours |
| Secundary driying | 25° C. | 12 hours |

Chronogram of temperature per phases.

At established intervals of time samples were taken and analyzed the content of residual humidity of the product, the content of IFN gamma and IFN alpha 2b (by ELISA), the biological activity, the purity by RP-HPLC and the appearance of the freeze-dried product as well as it reconstituted. The results are presented in the table 7.

TABLE 7

Data of residual humidity of the product, content of IFN gamma and IFN alpha 2b, the biological activity, purity by RP-HPLC. Temperature 5° C. FREEZE-DRIED FORMULATION: 1.4 MIU IFN gamma and 1.7 MIU IFN alpha 2b/vial.

| Time (month) | Residual humidity (%) | ELISA | | Antiviral Activity | Purity RP-HPLC | | | Description |
| | | IFNγ (μg/vial*) | IFNα (μg/vial*) | IU/vial* | Total (%) | IFNγ (%) | IFNα (%) | |
|---|---|---|---|---|---|---|---|---|
| Inicial | 1.4 | 315.8 | 21.9 | 2.51 | 97.8 | 90.6 | 7.2 | STI |
| 1 | — | 291.2 | 24.7 | 3.78 | 96.4 | 87.7 | 8.7 | STI |
| 3 | — | 307.5 | 23.5 | 3.17 | 97.7 | 87.9 | 9.8 | STI |
| 6 | 2.6 | 279.1 | 22.6 | 2.89 | 97.0 | 88.9 | 8.2 | STI |

*The filled volume was 0.5 mL/vial; STI: Uniform white lyophilized; after reconstitution, a transparent colorless solution, essentially free of particles.

Example 6

Freeze-Dried Formulation ($0.5 \times 10^6$ IU of IFN Gamma and $3.0 \times 10^6$ IU of IFN Alpha 2b Per Vial)

Composition: $1.0 \times 10^8$ UI, IFN alpha 2b $6.0 \times 10^8$ UI, di-hydrogen potassium phosphate 0.0802 g, di-sodium di-hydrated hydrogen phosphate 0.249 g, sacharose 4 g, glicine 0.8 g, Tween 20 0.03 g, polyetilenglycol 6000 1 g, water for injection sufficient quantity for 100 mL. The method of preparation was the same described in the freeze-dried formulation of the example 5.

At established intervals of time samples were taken and analyzed the content of residual humidity of the product, the content of IFN gamma and IFN alpha 2b (by ELISA), the biological activity, the purity by RP-HPLC and the appearance of the freeze-dried product as well as it reconstituted. The results are presented in the table 8.

TABLE 8

Data of residual humidity of the product, content of IFN gamma and IFN alpha 2b, the biological activity, purity by RP-HPLC. Temperature 5° C. FREEZE-DRIED FORMULATION: 0.5 MIU IFN gamma and 3.0 MIU IFN alpha 2b/vial.

| Time (month) | Residual humidity (%) | ELISA IFNγ (μg/vial*) | ELISA IFNα (μg/vial*) | Antiviral Activity IU/vial* | Antiviral total % | Purity RP-HPLC IFNα (%) | Purity RP-HPLC IFNγ (%) | Description |
|---|---|---|---|---|---|---|---|---|
| Inicial | 1.3 | 93.7 | 38.5 | 3.15 | 97.5 | 28.1 | 69.4 | STI |
| 1 | — | 104.5 | 43.9 | 4.41 | 96.8 | 29.5 | 67.3 | STI |
| 3 | — | 98.5 | 36.4 | 2.69 | 97.1 | 27.6 | 69.5 | STI |
| 6 | 1.9 | 108.2 | 44.0 | 3.91 | 96.9 | 28.8 | 68.1 | STI |

*The filled volume was 0.5 mL/vial; STI: Uniform white lyophilized; after reconstitution, a transparent colorless solution, essentially free of particles.

Example 7

Clinical Trial with the Stabilized Freeze-Dried Pharmaceutical Formulation ($0.5 \times 10^6$ IU of IFN Gamma and $3.0 \times 10^6$ IU of IFN Alpha 2B Per Vial). Application Intralesional in the CBC The stable freeze-dried pharmaceutical formulation described in the example 6 was employed in the execution of a triple blind, controlled, randomized clinical trial, that included 59 patients with clinical and histological diagnosis of CBC of any location and type of skin with lesions of a diameter less than four centimeters. The patients were assigned to three groups of treatment by randomization. The lesions were treated intralesional with the half of the doses of recombinant IFN alpha 2b ($1.5 \times 10^6$ IU/mL); or recombinant IFN gamma ($0.25 \times 10^6$ IU/mL) or the stable freeze-dried formulation ($0.5 \times 10^6$ IU of IFN gamma and $3.0 \times 10^6$ IU of IFN alpha 2b per vial), group I, II and III, respectively. The IFN were applied three times per weeks, during three consecutive weeks, continuing during 9 weeks, once a week, or until the total disappearance of the lesion, moment in which the clinical efficacy of the treatment was evaluated. The 9.5%, 35.3% and 5.3% of the lesions of the group with IFN alpha 2b, IFN gamma and the formulation ($0.5 \times 10^6$ IU of IFN gamma and $3.0 \times 10^6$ IU of IFN alpha 2b per vial), respectively diminished in less than 50% the size of the lesion. In the remainder lesions a 90.5%, 57.9% and 94.7% (group I, II and III, respectively) of objective response (total disappearance or decrease of more than the 50% of the initial size) was observed. None of the lesions progressed (to see table 9). In the stratum of the "patient that did not finish the treatment", a superiority of the treatment with the formulation that contains the recombinant IFNs gamma and alpha 2b with synergistic antiproliferative effect is observed (17% of difference with respect to the treatment with IFN alpha 2b and 27% of difference with respect to IFN gamma). In the stratum of the "patient with less than 11 weeks of treatment", a superiority of the formulation is observed. Approximately 30% of difference with respect to IFN gamma and 27% with respect to IFN alpha 2b. The proportion of complete response is higher (>40% of superiority with respect to IFN alpha 2b and >30% with respect to IFN gamma treatment). Patients with less than 12 injections, a 100% of favorable response were achieved (of them 50% of RC) in the group of the therapy with the formulation. In the other 2 treatment groups, the percentage of favorable response was of 67% (of them the 33.3% of RC), that is to say is achieved approximately a 33% of difference in favor of the combined therapy. See table 9.

TABLE 9

Evaluation of the clinical response stratifying according to time of treatment with the half dose FREEZE-DRIED FORMULATION: 0.5 MIU IFN gamma and 3.0 MIU IFN alpha 2b/vial.

| Variables | | IFN alfa | | IFN gamma | | Formulación | | P (Fisher) |
|---|---|---|---|---|---|---|---|---|
| Terminaron tratamiento | Completa | 7 (41.2%) | 17 (100%) | 4 (33.3%) | 9 (75.0%) | 8 (50%) | 16 (100%) | I-II p = 0.060 |
| | Parcial | 10 (58.8%) | | 5 (41.7%) | | 8 (50%) | | III-II p = 0.067 |
| | Estable | | 0 (0%) | 3 (25.0%) | | | 0 (0%) | |
| No terminaron tratamiento | Completa | 0 (0%) | 2 (50%) | 0 (0%) | 2 (40%) | 0 (0%) | 2 (66.7%) | I-II p = 1.000 |
| | Parcial | 2 (50%) | | 2 (28.6%) | | 2 (66.7%) | | III-II p = 1.000 |
| | Estable | | 2 (50%) | | 3 (60%) | | 1 (33.3%) | |

TABLE 9-continued

Evaluation of the clinical response stratifying according to time of treatment with the half dose FREEZE-DRIED FORMULATION: 0.5 MIU IFN gamma and 3.0 MIU IFN alpha 2b/vial.

| Variables | | IFN alfa | | IFN gamma | | Formulación | | P (Fisher) |
|---|---|---|---|---|---|---|---|---|
| Tiempo de tratamiento >= 11 semanas | Completa | 6 (37.5%) | 16 (100%) | 2 (20.0%) | 7 (70%) | 3 (27.3%) | 11 (100%) | I-II p = 0.046* |
| | Parcial | 10 (62.5%) | | 5 (50.0%) | | 8 (72.7%) | | III-II p = |
| | Estable | | 0 (0%) | | 3 (30%) | | 0 (0%) | 0.090 |
| Tiempo de tratamiento < 11 semanas | Completa | 1 (20%) | 3 (60%) | 2 (28.6%) | 4 (57.1%) | 5 (62.5%) | 7 (87.5%) | I-II p = 0.689 |
| | Parcial | 2 (40%) | | 2 (28.6%) | | 2 (25.0%) | | III-II p = |
| | Estable | | 2 (40%) | | 3 (42.9%) | | 1 (12.5%) | 0.230 |
| <12 inyecciones recibidas | Completa | 1 (33.3%) | 2 (66.7%) | 2 (33.3%) | 4 (66.7%) | 3 (50%) | 6 (100%) | I-II p = 1.000 |
| | Parcial | 1 (33.3%) | | 2 (33.3%) | | 3 (50%) | | III-II p = |
| | Estable | | 1 (33.3%) | | 2 (33.3%) | | 0 (0%) | 0.455 |
| >12 Inyecciones recibidas | Completa | 6 (33.3%) | 17 (94.4%) | 2 (18.2%) | 7 (63.6%) | 5 (38.5%) | 12 (92.3%) | I-II p = 0.054 |
| | Parcial | 11 (61.1%) | | 5 (45.4%) | | 7 (53.8%) | | III-II p = |
| | Estable | | 1 (5.6%) | | 4 (36.4%) | | 1 (7.7%) | 0.142 |

As we can observe in the table 10, with the stable freeze-dried formulation that contains the recombinant IFNs gamma and alpha 2b, it is possible to obtain clinical complete response in shorted period of time than with the interferons by separated, with a difference of approximately 4 weeks before with respect to IFN alpha.

TABLE 10

Evaluation of the time to the complete clinical response.

| Time to RC (Weeks) | IFN gamma (N = 17) | IFN alpha (N = 21) | Formulation (N = 19) | P (Kruskal-Wallis) |
|---|---|---|---|---|
| Median ± RQ | 9.0 ± 7.5 | 12.0 ± 1.0 | 8.5 ± 5.8 | 0.507 |

Treatment with the half dose freeze-dried formulation: 0.5 MU IFN gamma and 3.0 MIU IFN alpha 2b/vial.

In no treated case the formation of keloid was observed, on the contrary all the treated cases had a good scar formation of the lesion with normal sensibility, normal elasticity or slightly diminished and absence of dryness, fragility and harshness. With respect to the color, in the majority of the patients treated with the formulation was observed a normal coloring in the treated place (47.4%), the double of observed for the group with IFN alpha (28.6%). At the end of trial, in the group treated with the formulation a greater percentage of flat wounds was observed (63.2%) with respect to the group treated with IFN alpha alone 2b (52.4%) which is shown in the table 11.

TABLE 11

Esthetics evaluation at the end of treatment.

| Variables | | FN gamma (N = 17) | IFN alpha (N = 21) | Formulation (N = 19) |
|---|---|---|---|---|
| Color | Normochromy | 8 (47.1%) | 6 (28.6%) | 9 (47.4%) |
| | Slightly hypochromy | 1 (5.9%) | 4 (19%) | 6 (31.6%) |
| | Hypochromy | 1 (5.9%) | 2 (9.5%) | 1 (5.3%) |
| | Slightly hyperchromy | 7 (41.2%) | 8 (38.1%) | 3 (15.8%) |
| | Hyperchromy | — | 1 (4.8%) | — |
| Volumen | Flat lesion | 12 (70.6%) | 11 (52.4%) | 12 (63.2%) |
| | Slightly hypertrophy | 5 (29.4%) | 10 (47.6%) | 7 (36.8%) |

Treatment with the half dose freeze-dried formulation: 0.5 MIU IFN gamma and 3.0 MIU IFN alpha 2b/vial.

The combination of interferons did not potentate the adverse events, because there were not detected statistical differences between treatment groups, with respect to the production or intensity of them. In general, they were light (71.2%) or moderates and well tolerated. Themselves not adverse serious neither very serious events were presented. (Table 12).

TABLE 12

Frequency of adverse events (% with respect al total number of adverse events detected).

| Events | IFN gamma | IFN alpha | Formulation | Total |
|---|---|---|---|---|
| Fever | 31 (60.8%) | 15 (38.5%) | 11 (26.2%) | 57 (43.2%) |
| Myalgias | 2 (3.9%) | 15 (38.5%) | 13 (31.0%) | 30 (22.7%) |
| Chills | 10 (19.6%) | 5 (12.8%) | 9 (21.4%) | 24 (18.2%) |
| Astenia | 4 (7.8%) | 1 (2.6%) | 5 (11.9%) | 10 (7.6%) |
| Artralgias | — | 1 (2.6%) | 3 (7.1%) | 4 (3.0%) |
| Prurito | 3 (5.9%) | — | — | 3 (2.3%) |
| Weight loss | — | 2 (5.1%) | — | 2 (1.5%) |
| Allergy | 1 (2.0%) | — | — | 1 (0.8%) |
| Trombocytopenia | — | — | 1 (2.4%) | 1 (0.8%) |
| Leucopenia | — | — | 1 (2.4%) | 1 (0.8%) |
| Total de events | 39 (29.5%) | 39 (29.5%) | 43 (32.3%) | 133 (100%) |

Treatment with the half dose freeze-dried formulation: 0.5 MIU IFN gamma and 3.0 MIU IFN alpha 2b/vial.

As it can be observed in this table, the most frequent adverse events in each group of treatment were: fever (38.5%; 60.8% and 26.2%), myalgias (38.5%; 3.9% and 31%) and chills (12.8%; 19.6% and 21.4%) with IFN alpha, IFN gamma and the combination, respectively. The total of adverse events presented was slightly superior in the group of patients treated with IFN gamma.

In general, the combined treatment achieved a 32% of superiority of complete response, approximately 4 weeks before and with less than 25% injections with respect to the IFN alpha group. The combination did not promote adverse events and any recurrence was found during the follow-up one year after finalized the treatment for patients with complete clinical response. Since the cosmetic point of view, the result was very good resulting mostly in flat and normochromics wounds.

Example 8

Results of the Compasional Use of the Mixture of Recombinant IFNs Gamma and Alpha 2B in Patients with Skin Tumors, not Susceptible of Standard Treatment. Cases Report Patient 1

Patient EPR: HC: 302396 Age: 82 years, Sex: Male, personal pathological antecedent (APP): n/r Remitted to National Institute of Oncology and Radiology (INOR) 17 Oct. 2001 with tumor of the skin in the anterior region of thorax, had received electrofulguration treatment that after this grew in ulcerous form, having been surgically excision the 3 Jul. 2001. Result: Spinocellular carcinoma incompletely excised. The patient arrives with persistent tumoral lesion of 3 cm in the place of original tumor, with high edges. At physical observation did not present regional metastasic ganglion. Radiation therapy on the tumor was indicated, and ended it the 29 Jan. 2002: 60 co 50 Gy+X-Rays 12 Gy. Total dose per tumor was 62 gy.

A month later, the patient showed fixed tumor to the collarbone and at lower third of the esternocleidomastoide muscle. In short time, the tumor continued a fast growth, showing the 4 Mar. 2002 great-ulcerated wound of 10×8 cm on the internal third of the right collarbone, base of the neck and part of the sternum, all toward the previous part of the thorax. A surgical intervention was proposed to him. It was refused to be done a surgical intervention, because of his 82 years of age and to have high surgical risk. Then, a treatment with intra-lesional IFN was recommended.

The tumor with high size (12.5×9 cm and 1-1.5 cm in thickness), was fixed to bone and muscle. The IFN application was planned in three sectors of perimeter. Each sector was infiltrated with 1.5 mL of solution in approximately 5 cm$^3$ of tissue (1.5×1.5×1.5) to a dose of 0.5×10$^6$ IU of IFN gamma+6×10$^6$ IU of IFN alpha 2b in 6 mL of water for injection, three times per week for three weeks (FIG. 7a). After the fifth application of the product (second week) is decided to applied a higher dose of IFN gamma (double, 1×10$^6$ IU). The dose escalation was proposed trying to obtain a better result of a so large tumor, because of the absence of adverse effects in the previous dosage, and on the prior information of the clinical study where the synergistic effect of both interferons was shown.

Overall, the patient received 27 applications for a total dose of 25×10$^6$ IU of IFN gamma+162×10$^6$ IU of IFN alpha 2b in two months of treatment. In the fifth application, it was appreciated a leveling of the edge of the wound to the level of the normal skin, (FIG. 7b). A month after beginning the treatment, the patient refers intense pain of the right upper member being observed infiltration of the brachial nervous plexus, exposition, necrosis and fracture of the collarbone. At application #20 was observed that in the places injected stopped the tumoral growth, but not thus in the center of the tumor where grew in lobular-like shape, (FIG. 7c). This condition was observed even at the application 24. Besides appeared sepsis and necrosis in the center of the tumoral ulcer. Exactly two months after started the treatment (application #27) the patient suffered intense arterial bleeding by infiltration of the artery subclavia; the hemoglobin of the patient lowered to 80 g/L, and the treatment was interrupted for 15 days, at the end of which returned due to a continuing bleeding and to have progressive asthenia. The patient died two months later by arterial break. The places injected were maintained without tumor growth. In the first eight applications, some adverse events were registered like fever (39° C.), chills, perilesional erythema and asthenia, but all of slightly intensities and short term. Conclusions: Clinical response in the places injected was reached, lasting by at least two months, adverse effects were without importance.

Patient 2

Patient LGR: HC: 158390 Age: 65 years Sex: Female, APP: n/r. Patient that suffers of multiple carcinomas based on all the face. The patient was intervened surgically and radiated several times in the lower eyelid of the left eye with grafts. Now shows tumor recurrence of 5 mm of diameter in the edge of the eyelid and another flat scar-like wound under the eyelid toward the cheekbone, (FIG. 8a). The alternative of treatment would be a new surgery with the objections to be a case already multi-treated. In the upper eyelid of the same eye has another basal carcinoma of 7 mm that has not been previously treated.

8 May 2002 is proposed the treatment with intralesional IFN (0.5×10$^6$ IU of IFN gamma+3×10$^6$ IU of IFN alpha 2b) in 4 mL, three times for week for three weeks. Overall, the patient received 10 applications for a total dose of 35×10$^6$ IU of interferon (5×10$^6$ IU of IFN gamma+30×10$^6$ IU of IFN alpha 2b). In the quarter infiltration, the scar-like wound disappeared and in the eyelid had an ulcer necrotized in the place of the tumor, (FIG. 8b). Two months after the treatment, not tumor in the eyelid and disappearance of the scar-like flat wound of the cheekbone is observed (FIG. 8c). A local-regional effect was obtained. It was observed a reduction in 50% of the basal carcinoma of the upper eyelid of the left eye that was not treated directly with IFN that then was surgical excised. Three years later the patient remains still controlled of the infiltrated lesions with IFN. Some adverse events of light intensities and of short term were registered like fever (39° C.), chills and chemosis in the treated eye that was alleviated with cold compresses.

Conclusions: Patient with complete clinical response until August of the 2005 (last control), minimum adverse effects.

Example 9

Freeze-Dried Formulation (0.5×10$^6$ IU of IFN Gamma and 10×10$^6$ $^7$U of IFN Alpha 2B Per Vial)

Composition: IFN gamma 1.0×10$^8$ IU, IFN alpha 2b 20×10$^8$ IU, potassium di-hydrogen phosphate 0.0802 g, di-sodium di-hydrated hydrogen phosphate 0.249 g, sacharose 4 g, glicine 0.8 g, Tween 20 0.03 g, polyetilenglycol 6000 1 g, water for injection sufficient quantity for 100 mL.

The method of preparation was the same that was described in the freeze-dried formulation of the example 5.

At established intervals of time samples were taken and analyzed the content of residual humidity of the product, the content of IFN gamma and IFN alpha 2b (by ELISA), the biological activity, the purity by RP-HPLC and the appearance of the freeze-dried product as well as it reconstituted. The results are presented in the table 13.

TABLE 13

Data of residual humidity of the product, content of IFN gamma and IFN alpha 2b, the biological activity, and purity by RP-HPLC. Temperature 5° C. FREEZE-DRIED FORMULATION: 0.5 MIU IFN gamma and 10.0 MIU IFN alpha 2b/vial.

| | | ELISA | | Activity | | Purity RP-HPLC | | |
|---|---|---|---|---|---|---|---|---|
| Time (month) | Residual Humidity % | IFNγ (μg/vial*) | IFNα (μg/vial*) | Antiviral (IU/vial*) | Total (%) | IFNγ (%) | IFNα (%) | Description |
| Inicial | 0.9 | 94.0 | 142.2 | 12.90 | 98.8 | 43.7 | 55.1 | STI |
| 1 | — | 105.5 | 133.2 | 8.37 | 97.7 | 40.8 | 56.9 | STI |
| 3 | — | 102.1 | 129.4 | 11.55 | 97.6 | 43.0 | 54.5 | STI |
| 6 | 1.7 | 91.7 | 137.1 | 9.13 | 95.4 | 39.4 | 57.0 | STI |

*The filled volume was 0.5 mL/vial; STI: Uniform white lyophilized; after reconstitution, a transparent colorless solution, essentially free of particles.

Example 10

Employment of Stable Freeze-Dried Formulation Composed by 0.5 MIU IFN Gamma and 10.0 MIU IFN Alpha 2b/Vial in Combination with Cisplatin. Report of case Patient 3

Patient JGA: HC: Age: 33 years, Sex: Male, APP: Patient n/r recorded in the INOR with a carcinoma of basal cells that penetrates the internal angle of the left eye, with several surgical interventions, and radiated. Now, the patient has a tumor ulcerated that arrives to the bones of the base of the skull (FIG. 9a). Verified by axial computerized tomography (TAC) is observed cavity in the own bones of the nose and of the internal wall of the orbit, unbearable fetidness that leaves for the left nostril and purulent yellow secretion at the same place.

Due to the extension of the wound was decided to do a combined treatment with systemic chemotherapy with cysplatin to dose of 6 cycles with intervals of 21 days and at same time the formulation (0.5 MIU IFN gamma and 10.0 MIU IFN alpha 2b/vial) infiltrated locally 3 times for week for three weeks.

At the end of the third application, already important partial clinical response was observed, that permit the palpebral opening and the decrease of the fetidness. It was present at the same time chemosis of moderate intensity. A complete clinical response is appreciated after a month. This response is maintained until the end of chemotherapy. The adverse events were few, something fever and chills and pain referred in the place of the scar of the wound. A year later the patient maintains the complete clinical response (FIG. 9b).

Example 11

Liquid Stable Pharmaceutical Formulation ($1.4 \times 10^6$ IU of IFN Gamma and $1.7 \times 10^6$ IU of IFN Alpha 2b Per Vial)

Composition: IFN gamma $2.8 \times 10^8$ IU, IFN alpha 2b $3.4 \times 10^8$ IU, sodium acetate 0.708 g, acetic acid 0.079 mL, Tween 20 0.01 g, manitol 5 g, water for injection sufficient quantity for 100 mL.

All the components except the interferons were measured and suspended with water for injection. The pH of the solution was checked and, if is necessary, adjusted to value of 5.5±0.2 with acetic acid diluted (1:2) or with 1 M of NaOH. The active pharmaceutical ingredients of recombinant IFN gamma and IFN alpha 2b were added and diluted to the appropriate concentration.

The solution was filtered in sterile condition. The vials were filled with the formulation and covered and sealed in a class 100 area. Finally, the product is stored between 2 and 8° C. Several samples were taken from the manufactured formulation, and stored at 8° C. and 2° C. for a period of six months.

At established intervals of time samples were taken and analyzed the content of residual humidity of the product, the content of IFN gamma and IFN alpha 2b (by ELISA), the biological activity, the purity by RP-HPLC and the appearance of the freeze-dried product as well as it reconstituted. The results are presented in the table 14.

TABLE 14

Data of pH of the product, content of IFN gamma and IFN alpha 2b, the biological activity, and purity by RP-HPLC. Temperature 5° C. LIQUID FORMULATION: 1.4 MIU IFN gamma and 1.7 MIU IFN alpha 2b/vial.

| | | ELISA | | Activity | | Purity RP-HPLC | | |
|---|---|---|---|---|---|---|---|---|
| Time (months) | pH | IFNγ (μg/vial*) | IFNα (μg/vial*) | Antiviral IU/vial* | Total (%) | IFNγ (%) | IFNα (%) | Description |
| Inicial | 5.58 | 305.2 | 24.9 | 3.66 | 96.9 | 88.1 | 8.8 | STI |
| 1 | 5.43 | 279.1 | 21.2 | 3.21 | 97.2 | 87.9 | 9.3 | STI |

TABLE 14-continued

Data of pH of the product, content of IFN gamma and IFN alpha 2b, the biological activity, and purity by RP-HPLC. Temperature 5° C. LIQUID FORMULATION: 1.4 MIU IFN gamma and 1.7 MIU IFN alpha 2b/vial.

| Time | | ELISA | | Activity | | Purity RP-HPLC | | |
|---|---|---|---|---|---|---|---|---|
| (months) | pH | IFNγ (µg/vial*) | IFNα (µg/vial*) | Antiviral IU/vial* | Total (%) | IFNγ (%) | IFNα (%) | Description |
| 3 | 5.56 | 285.4 | 20.7 | 2.47 | 95.8 | 89.7 | 7.1 | STI |
| 6 | 5.45 | 293.0 | 23.9 | 3.39 | 95.5 | 88.1 | 8.4 | STI |

*The filled volume was 0.5 mL/vial; STI: Uniform white lyophilized; after reconstitution, a transparent colorless solution, essentially free of particles.

Example 12

Liquid Stable Pharmaceutical Formulation (0.5×10$^6$ IU of IFN Gamma and 3.0×10$^6$ IU of IFN Alpha 2b Per Vial)

Composition: IFN gamma 2.0×10$^8$ IU, IFN alfa 2b 12.0×10$^8$ IU, sodium acetate 0.708 g, acetic acid 0.079 mL, Tween 20 0.01 g, manitol 5 g, water for injection sufficient quantity for 100 mL.

The method of preparation was the same that was described in the freeze-dried formulation of the example 11.

At established intervals of time samples were taken and analyzed the content of residual humidity of the product, the content of IFN gamma and IFN alpha 2b (by ELISA), the biological activity, the purity by RP-HPLC and the appearance of the freeze-dried product as well as it reconstituted. The results are presented in the table 15.

Example 13

Liquid Stable Pharmaceutical Formulation (0.5×10$^6$ IU De IFN Gamma and 10×10$^6$ IU De IFN Alpha 2b Per Vial)

Composition: IFN gamma 2.0×10$^8$ IU, IFN alpha 2b 40×10$^8$ IU, sodium acetate 0.708 g, acetic acid 0.079 mL, Tween 20 0.01 g, manitol 5 g, water for injection sufficient quantity for 100 mL.

The method of preparation was the same that was described in the freeze-dried formulation of the example 11.

At established intervals of time samples were taken and analyzed the content of residual humidity of the product, the content of IFN gamma and IFN alpha 2b (by ELISA), the biological activity, the purity by RP-HPLC and the appearance of the freeze-dried product as well as it reconstituted. The results are presented in the table 16.

TABLE 15

Data of pH of the product, content of IFN gamma and IFN alpha 2b, the biological activity, and purity by RP-HPLC. Temperature 5° C. LIQUID FORMULATION: 0.5 MUI IFN gamma and 3.0 MIU IFN alpha 2b/vial.

| Time | | ELISA | | Activity | | Purity P-HPLC | | |
|---|---|---|---|---|---|---|---|---|
| (months) | pH | IFNγ (µg/vial*) | IFNα (µg/vial*) | Antiviral IU/vial* | Total (%) | IFNγ (%) | IFNα (%) | Description |
| Initial | 5.55 | 109.4 | 38.2 | 4.25 | 97.6 | 58.3 | 29.3 | STI |
| 1 | 5.37 | 103.7 | 39.5 | 2.73 | 97.1 | 59.8 | 27.3 | STI |
| 3 | 5.49 | 95.0 | 42.9 | 3.35 | 97.3 | 70.2 | 27.1 | STI |
| 6 | 5.58 | 94.9 | 36.2 | 3.91 | 96.8 | 58.5 | 28.3 | STI |

*The filled volume was 0.5 mL/vial; STI: Uniform white lyophilized; after reconstitution, a transparent colorless solution, essentially free of particles.

TABLE 16

Data of pH of the product, content of IFN gamma and IFN alpha 2b,
the biological activity, and purity by RP-HPLC. Temperature 5° C. LIQUID
FORMULATION: 0.5 MIU IFN gamma and 10.0 MIU IFN alpha 2b/vial.

| Time (months) | pH | ELISA IFNγ (μg/vial*) | ELISA IFNα (μg/vial*) | Activity Antiviral IU/vial* | Total (%) | Purity RP-HPLC IFNγ (%) | Purity RP-HPLC IFNα (%) | Description |
|---|---|---|---|---|---|---|---|---|
| Initial | 5.53 | 91.9 | 138.2 | 12.41 | 98.0 | 39.1 | 58.9 | STI |
| 1 | 5.57 | 93.7 | 121.5 | 8.73 | 97.5 | 41.7 | 55.9 | STI |
| 3 | 5.49 | 105.0 | 142.9 | 9.46 | 95.8 | 38.2 | 58.6 | STI |
| 6 | 5.51 | 99.8 | 134.7 | 10.93 | 97.5 | 42.5 | 42.5 | STI |

*The filled volume was 0.5 mL/vial; STI: Uniform white lyophilized; after reconstitution, a transparent colorless solution, essentially free of particles.

Example 14

Semisolid Pharmaceutical Formulation (0.16×10⁶ IU of IFN Gamma and 1.0×10⁶ IU of IFN Alpha 2b Per Gram of Semisolid)

Pharmaceutical formulation for topic application, preferably as a cream, unguent or gel. The pharmaceutical preparation contains recombinant interferon gamma and alpha interferon 2 as active principle. The composition is of $1.6 \times 10^7$ IU of IFN gamma and of $1 \times 10^8$ IU of IFN alpha 2b, sufficient quantity for 100 grams of semisolid.

Preparation of Cream:

To Prepare the Cream Melts the Solid Vaseline and the cethylic alcohol at 75° C. and mixed with constant agitation, maintained to the end of the process. Once homogenized Tween 60 is incorporated to the mixture. On the other hand, the methyl- and propyl-paraben is dissolved in water at 90° C. and is incorporated to the previous mixture when the temperature have diminished until 75° C. Subsequently the emulsion is cooling slowly until 37° C. and is incorporated the water solution that contains the recombinant IFN gamma and IFN alpha 2b. The resultant cream is stored to 4° C. in 15 g tubes (to see table 17).

TABLE 17

Ingredients of the cream formulation.

| Ingredients | % |
|---|---|
| IFN γ | 2.2 |
| IFNα 2b | 0.58 |
| Cethylic Alcohol | 4 |
| Vaseline | 10 |
| Tween 60 | 2 |
| Methyl-, propyl-paraben | 0.2 |
| Destiled water c.s.p | 81.2 |

Preparation of Unguent:

In a container, the parabens are dissolved in the water at 90° C. and then left to chill to 37° C. In another container the liquid petrolate and the Span 20 are mixed with constant agitation. Subsequently, the content of both containers is mixed and when the temperature have diminished under 37° C. is incorporated the recombinant IFN gamma and IFN alpha 2b, maintaining the constant agitation. Then it is incorporated the white petrolate until achieving a homogenization. The resultant unguent is stored to 4° C. in 15 g tubes (to see table 18).

TABLE 18

Ingredients of the unguent formulation.

| Ingredients | % |
|---|---|
| IFN γ | 2.2 |
| IFNα 2b | 0.58 |
| White solid petrolate | 60 |
| Heavy liquid petrolate | 10 |
| Span 20 | 3 |
| Methyl- propyl-paraben | 0.2 |
| Destiled water c.s.p | 24.02 |

Preparation of Gel:

The EDTA, Parabens and Alcohol are Dissolved in Separated containers and then is added the propylenglycol. Then these solutions with constant agitation are mixed and is incorporated slowly the carbopol 940 with vigorous agitation until obtaining a murky dispersion without presence of lumps. It is prepared separated, in an adequate container, a 1N sodium hydroxide solution and is added slowly with agitation to the dispersion that contains the remainder of the components of the formulation. Subsequently the IFN gamma and IFN alpha 2b are incorporated with gentle agitation. Once the gel is formed is bottled in 15 g tubes at 4° C. (to see table 19).

TABLE 19

Ingredients of the gel formulation.

| Ingredients | % |
|---|---|
| IFN γ | 2.2 |
| IFNα 2b | 0.58 |
| Carbopol 940 | 0.5 |
| Propylenglycol | 10 |
| Methylparaben and Propylparaben | 0.2 |
| Sodium hydroxide | 0.2 |
| Disodium calcium ethylenediaminetetraacetate (EDTA) | 0.01 |
| Ethanol | 2 |
| Destiled water c.s.p | 84.31 |

The invention claimed is:

1. A stabilized liquid or freeze dried composition for the treatment of benign, non-physiological or malignant solid tumors in a human, said composition comprising a mixture per vial of synergistic proportions of recombinant gamma interferon, recombinant alpha interferon, succinate and trehalose, wherein said composition maintains a pH between 4.9 and 7.4, and wherein the synergistic proportions of interferons are $1.4 \times 10^8$ IU gamma interferon and $1.7 \times 10^8$ IU alpha interferon, or $1.0 \times 10^8$ IU gamma interferon and $20.0 \times 10^8$ IU alpha interferon, or $0.5 \times 10^8$ IU gamma interferon and $3.0 \times 10^8$ IU alpha interferon.

2. The composition according to claim 1, further comprising at least one component selected from non-reducing sugar compounds, amino acids, surfactants, stabilizer polymers, chelating/anti-oxidant compounds and isotonizing agents.

3. The composition according to claim 2, wherein the surfactant is in a concentration range between 0.01 and 1 mg/mL; wherein the amino acid is in a concentration range between 1 and 20 mg/mL; and wherein the stabilizer polymer is in a concentration range between 5 and 50 mg/mL.

4. The composition according to claim 1, for the treatment of laryngeal carcinoma, laryngeal papillomatosis, lipoma, epidermoid cyst, intradermic cyst, liposarcoma, neurofibroma, sebaceous hyperplasia, cavernous hemagioma, hepatocellular adenoma, focal nodular hyperplasia, astrocytoma, multiform glioblastoma, ependymomas, ganglioneuromas, juvenile pylocytic astrocytoma, mixed gliomas, oligodendrogliomas, optic nerve glioma, cordomas, craniopharyngiomas, meduloblastomas, meningiomas, pineal tumors, pituitary adenomas, primitive neuroectodermal tumors, acoustic neuromas, vascular tumors, meningeal carcinomatosis, neurofibromatosis, brain pseudotumors, tuberose sclerosis, metastatic brain tumors, cherry like angiomas, sebaceous gland hyperplasia, basal cell carcinoma, squamous cell carcinoma, dermatofibroma, pyogenic granuloma, dermic nevus, seborrheic keratosis, and/or actinic keratosis.

5. The composition according to claim 1, to be applied intramuscular, intratumoral or perilesional.

6. The composition according to claim 1, wherein the composition is stable during prolonged storage.

7. The composition according to claim 1, wherein the composition is stable during freezing-thawing cycles.

* * * * *